United States Patent [19]
Chen et al.

[11] Patent Number: 6,013,786
[45] Date of Patent: Jan. 11, 2000

[54] MDM2-SPECIFIC ANTISENSE OLIGONUCLEOTIDES

[75] Inventors: Jiandong Chen, Metairie, La.; Sudhir Agrawal, Shrewsbury, Mass.; Ruiwen Zhang, Marietta, Ga.

[73] Assignee: Hybridon, Inc., Cambridge, Mass.

[21] Appl. No.: 09/073,567

[22] Filed: May 6, 1998

Related U.S. Application Data

[63] Continuation-in-part of application No. 08/916,384, Aug. 22, 1997.

[51] Int. Cl.$^7$ .................................................. C07H 21/04
[52] U.S. Cl. ..................... 536/24.5; 536/23.1; 536/24.3; 536/24.31
[58] Field of Search ................................ 536/23.1, 24.3, 536/24.31, 24.5

[56] References Cited

U.S. PATENT DOCUMENTS

| | | | |
|---|---|---|---|
| 5,149,797 | 9/1992 | Pederson et al. | 536/23.1 |
| 5,411,860 | 5/1995 | Vogelstein | 435/6 |
| 5,550,023 | 8/1996 | Kinzler et al. | 435/7.1 |
| 5,652,355 | 7/1997 | Metelev et al. | 536/24.5 |
| 5,652,356 | 7/1997 | Agrawal | 536/24.5 |

FOREIGN PATENT DOCUMENTS

| | | |
|---|---|---|
| WO 93/20238 | 10/1993 | WIPO . |
| WO 97/09343 | 3/1997 | WIPO . |

OTHER PUBLICATIONS

Chen et al. *Proc. Natl. Acad. Sci. U.S.A.* 95:195–200 (1998).
Pon. *Methods in Molec. Biol.* 20:465 (1993).
Wu et al. *Genes Dev.* 7:1126–1132 (1993).
Sager et al. *Science.* 246:1406–1412 (1989).
Chen et al. *Mol. Cell. Biol.* 16:2445–2452 (1996).
Chen et al. *Mol. Cell. Biol.* 13:(7)4107–4114 (1993).
Marshall et al. *Cell.* 64:313–326 (1991).
Levine et al. *Nature.* 351:453–456 (1991).
Lane, *Br. Med. Bull.* 50:(3)582–599 (1994).
Lowe et al. *Cell.* 74:957–967 (1993).
Lowe et al. *Science.* 266:807–810 (1994).
Kastan et al. *Cancer Res.* 51:6304–6311 (1991).
Fritsche et al. *Oncogene.* 8:307–318 (1993).
Cahill–Snyder et al. *Somatic Cell. Mol. Genet.* 13:235–244 (1987).
Fakharadeh et al. *EMBO J.* 10:1565–1569 (1991).
Cordon–Cardo et al. *Cancer Res.* 54:794–799 (1994).
Ladanyi et al. *Cancer Res.* 53:16–18 (1993).
Oliner et al. *Nature.* 358:80–83 (1992).
Reifenberger et al. *Cancer Res.* 53:2736–2739 (1993).
Sheikh et al. *Cancer Res.* 53:3226–3228 (1993).
Bueso–Ramos et al. *Blood.* 82:2617–2623 (1993).
Watanabe et al. *Blood.* 84:3158–3165 (1994).
Xiao et al. *Nature.* 375:694–698 (1995).
Marechal et al. *Mol. Cell. Biol.* 14:7414–7419 (1994).
Kondo et al. *Oncogene.* 10:(10)2001–2006 (1995).
Kondo et al. *Br. J. Cancer.* 74:(8)1263–1268 (1996).
Mayo et al. *Cancer Res.* 57:5013–5016 (1997).
Shieh et al. *Cell.* 91:325–334 (1997).
Hollstein et al. *Nucleic Acids Res.* 22:3551–3555 (1994).
Kaghad et al. *Cell.* 90:809–819 (1997).
Moll et al. *Proc. Natl. Acad. Sci. U.S.A.* 92:4407–4411 (1995).
Goldman et al. *Am. J. Pathol.* 148:1381–1385 (1996).
Coopes et al. *Cancer Invest.* 12(1):57–65 (1994).
Levine. *Bioessays.* 12(2):60–66 (1990).
Weinberg et al. *Neur.* 11:191–196 (1991).
Leach et al. *Cancer Res.* 53:2231–2234 (1993).
Matsumaura et al. *Oncology.* 53:308–312 (1996).
Xiao et al. *Nature.* 375:695–698 (1995).
Elenbaas et al. *Mol. Med.* 2:(4)439–451 (1996).
Shaulian. *Oncogene.* 15:2717–2725 (1997).
Baker et al. *Science.* 249:912–915 (1990).
Zhao et al. *Biochem Pharm.* 51:173–182 (1996).
Agrawal et al. *Antisense Research and Applications.* S. Crooke, ed. Heidelberg: Spirnger–Verlag, 1997, pp. 525–543.
Zhang et al. *Biochem Pharm.* 50:545–556 (1995).
Zhang et al. *Biochem. Pharm.* 49:929–939 (1995).
Harvey et al. *Genes Dev.* 5:2375–2385 (1991).
Harlow et al. *J. Virol.* 39:861–869 (1981).
Takahashi et al. *Mol. Carcinog.* 8:58–66 (1993).
Zhang et al. *Intl. J. Oncol.* 10:1147–1156 (1997).
Cai et al. *Intl. J. Oncol.* 10:953–960 (1997).
Martin et al. *Nature.* 375:691–694 (1995).
Williams et al. *Nature Genet.* 7:480–484 (1994).

*Primary Examiner*—Nancy Degen
*Assistant Examiner*—Andrew Wang
*Attorney, Agent, or Firm*—McDonnell Boehnen Hulbert & Berghoff

[57] ABSTRACT

The invention provides methods to activate tumor suppressors. The invention further provides antisense oligonucleotides complementary to a portion of the MDM2-encoding RNA and methods for using such antisense oligonucleotides as analytical and diagnostic tools, as potentiators of transgenic animal studies and for gene therapy approaches, and as potential therapeutic agents. The invention also provides methods to augment and synergistically activate a tumor suppressor in conjunction with the use of a DNA-damage inducing agent.

18 Claims, 21 Drawing Sheets

```
GCACCGCGCG AGCTTGGCTG CTTCTGGGGC CTGTGTGGCC CTGTGTGTCG GAAAGATGGA
GCAAGAAGCC GAGCCCGAGG GGCGGCCGCG ACCCTCTGA CCGAGATCCT GCTGCTTTCG
CAGCCAGGAG CACCGTCCCT CCCCGGATTA GTGCGTACGA GCGCCCAGTG CCCTGGCCCG
GAGAGTGGAA TGATCCCCGA GGCCCAGGGC GTCGTGCTTC CGCAGTAGTC AGTCCCCGTG
AAGGAAACTG GGGAGTCTTG AGGGACCCCC GACTCCAAGC GCGAAAACCC CGGATGGTGA
GGAGCAGGCA AATGTGCAAT ACCAACATGT CTGTACCTAC TGATGGTGCT GTAACCACCT
CACAGATTCC AGCTTCGGAA CAAGAGACCC TGGTTAGACC AAAGCCATTG CTTTTGAAGT
TATTAAAGTC TGTTGGTGCA CAAAAAGACA CTTATACTAT GAAAGAGGTT CTTTTTTATC
TTGGCCAGTA TATTATGACT AAACGATTAT ATGATGAGAA GCAACAACAT ATTGTATATT
GTTCAAATGA TCTTCTAGGA GATTTGTTTG GCGTGCCAAG CTTCTCTGTG AAAGAGCACA
GGAAAATATA TACCATGATC TACAGGAACT TGGTAGTAGT CAATCAGCAG GAATCATCGG
ACTCAGGTAC ATCTGTGAGT GAGAACAGGT GTCACCTTGA AGGTGGGAGT GATCAAAAGG
ACCTTGTACA AGAGCTTCAG GAAGAGAAAC CTTCATCTTC ACATTTGGTT TCTAGACCAT
CTACCTCATC TAGAAGGAGA GCAATTAGTG AGACAGAAGA AAATTCAGAT GAATTATCTG
GTGAACGACA AAGAAAACGC CACAAATCTG ATAGTATTTC CCTTTCCTTT GATGAAAGCC
TGGCTCTGTG TGTAATAAGG GAGATATGTT GTGAAAGAAG CAGTAGCAGT GAATCTACAG
GGACGCCATC GAATCCGGAT CTTGATGCTG GTGTAAGTGA ACATTCAGGT GATTGGTTGG
ATCAGGATTC AGTTTCAGAT CAGTTTAGTG TAGAATTTGA AGTTGAATCT CTCGACTCAG
AAGATTATAG CCTTAGTGAA GAAGGACAAG AACTCTCAGA TGAAGATGAT GAGGTATATC
AAGTTACTGT GTATCAGGCA GGGGAGAGTG ATACAGATTC ATTTGAAGAA GATCCTGAAA
TTTCCTTAGC TGACTATTGG AAATGCACTT CATGCAATGA AATGAATCCC CCCCTTCCAT
CACATTGCAA CAGATGTTGG GCCCTTCGTG AGAATTGGCT TCCTGAAGAT AAAGGGAAAG
ATAAAGGGGA AATCTCTGAG AAAGCCAAAC TGGAAAACTC AACACAAGCT GAAGAGGGCT
TTGATGTTCC TGATTGTAAA AAAACTATAG TGAATGATTC CAGAGAGTCA TGTGTTGAGG
AAAATGATGA TAAAATTACA CAAGCTTCAC AATCACAAGA AAGTGAAGAC TATTCTCAGC
CATCAACTTC TAGTAGCATT ATTTATAGCA GCCAAGAAGA TGTGAAAGAG TTTGAAAGGG
AAGAAACCCA AGACAAAGAA GAGAGTGTGG AATCTAGTTT GCCCCTTAAT GCCATTGAAC
CTTGTGTGAT TTGTCAAGGT CGACCTAAAA ATGGTTGCAT TGTCCATGGC AAAACAGGAC
ATCTTATGGC CTGCTTTACA TGTGCAAAGA AGCTAAAGAA AAGGAATAAG CCCTGCCCAG
TATGTAGACA ACCAATTCAA ATGATTGTGC TAACTTATTT CCCCTAGTTG ACCTGTCTAT
AAGAGAATTA TATATTTCTA ACTATATAAC CCTAGGAATT TAGACAACCT GAAATTTATT
CACATATATC AAAGTGAGAA AATGCCTCAA TTCACATAGA TTTCTTCTCT TTAGTATAAT
TGACCTACTT TGGTAGTGGA ATAGTGAATA CTTACTATAA TTTGACTTGA ATATGTAGCT
CATCCTTTAC ACCAACTCCT AATTTTAAAT AATTTCTACT CTGTCTTAAA TGAGAAGTAC
TTGGTTTTTT TTTTCTTAAA TATGTATATG ACATTTAAAT GTAACTTATT ATTTTTTTTG
AGACCGAGTC TTGCTCTGTT ACCCAGGCTG GAGTGCAGTG GGTGATCTTG GCTCACTGCA
AGCTCTGCCC TCCCGGGTT CGCACCATTC TCCTGCCTCA GCCTCCCAAT TAGCTTGGCC
TACAGTCATC TGCCACCACA CCTGGCTAAT TTTTTGTACT TTTAGTAGAG ACAGGGTTTC
ACCGTGTTAG CCAGGATGGT CTCGATCTCC TGACCTCGTG ATCCGCCCAC CTCGGCCTCC
CAAAGTGCTG GGATTACAGG CATGAGCCAC CG
```

FIG. 1A

```
GAGGAGCCGC CGCCTTCTCG TCGCTCGAGC TCTGGACGAC CATGGTCGCT CAGGCCCCGT
CCGCGGGGCC TCCGCGCTCC CCGTGAAGGG TCGGAAGATG CGCGGGAAGT AGCAGCCGTC
TGCTGGGCGA GCGGGAGACC GACCGGACAC CCCTGGGGGA CCCTCTCGGA TCACCGCGCT
TCTCCTGCGG CCTCCAGGCC AATGTGCAAT ACCAACATGT CTGTGTCTAC CGAGGGTGCT
GCAAGCACCT CACAGATTCC AGCTTCGGAA CAAGAGACTC TGGTTAGACC AAAACCATTG
CTTTTGAAGT TGTTAAAGTC CGTTGGAGCG CAAAACGACA CTTACACTAT GAAAGAGATT
ATATTTTATA TTGGCCAGTA TATTATGACT AAGAGGTTAT ATGACGAGAA GCAGCAGCAC
ATTGTGTATT GTTCAAATGA TCTCCTAGGA GATGTGTTTG GAGTCCCGAG TTTCTCTGTG
AAGGAGCACA GGAAAATATA TGCAATGATC TACAGAAATT TAGTGGCTGT AAGTCAGCAA
GACTCTGGCA CATCGCTGAG TGAGAGCAGA CGTCAGCCTG AAGGTGGGAG TGATCTGAAG
GATCCTTTGC AAGCGCCACC AGAAGAGAAA CCTTCATCTT CTGATTTAAT TTCTAGACTG
TCTACCTCAT CTAGAAGGAG ATCCATTAGT GAGACAGAAG AGAACACAGA TGAGCTACCT
GGGGAGCGGC ACCGGAAGCG CCGCAGGTCC CTGTCCTTTG ATCCGAGCCT GGGTCTGTGT
GAGCTGAGGG AGATGTGCAG CGGCGGCACG AGCAGCAGTA GCAGCAGCAG CAGCGAGTCC
ACAGAGACGC CCTCGCATCA GGATCTTGAC GATGGCGTAA GTGAGCATTC TGGTGATTGC
CTGGATCAGG ATTCAGTTTC TGATCAGTTT AGCGTGGAAT TTGAAGTTGA GTCTCTGGAC
TCGGAAGATT ACAGCCTGAG TGACGAAGGG CACGAGCTCT CAGATGAGGA TGATGAGGTC
TATCGGGTCA CAGTCTATCA GACAGGAGAA AGCGATACAG ACTCTTTTGA AGGAGATCCT
GAGATTTCCT TAGCTGACTA TTGAAGTGT ACCTCATGCA ATGAAATGAA TCCTCCCCTT
CCATCACACT GCAAAAGATG CTGGACCCTT CGTGAGAACT GGCTTCCAGA CGATAAGGGG
AAAGATAAAG TGGAAATCTC TGAAAAAGCC AAACTGGAAA ACTCAGCTCA GGCAGAAGAA
GGCTTGGATG TGCCTGATGG CAAAAAGCTG ACAGAGAATG ATGCTAAAGA GCCATGTGCT
GAGGAGGACA GCGAGGAGAA GGCCGAACAG ACGCCCTGT CCCAGGAGAG TGACGACTAT
TCCCAACCAT CGACTTCCAG CAGCATTGTT TATAGCAGCC AAGAAAGCGT GAAAGAGTTG
AAGGAGGAAA CGCAGCACAA AGACGAGAGT GTGGAATCTA GCTTCTCCCT GAATGCCATC
GAACCATGTG TGATCTGCCA GGGGCGGCCT AAAAATGGCT GCATTGTTCA CGGCAAGACT
GGACACCTCA TGTCATGTTT CACGTGTGCA AAGAAGCTAA AAAAAGAAA CAAGCCCTGC
CCAGTGTGCA GACAGCCAAT CCAAATGATT GTGCTAAGTT ACTTCAACTA GCTGACCTGC
TCACAAAAAT AGAATTTTAT ATTTCTAACT
```

FIG. 1B

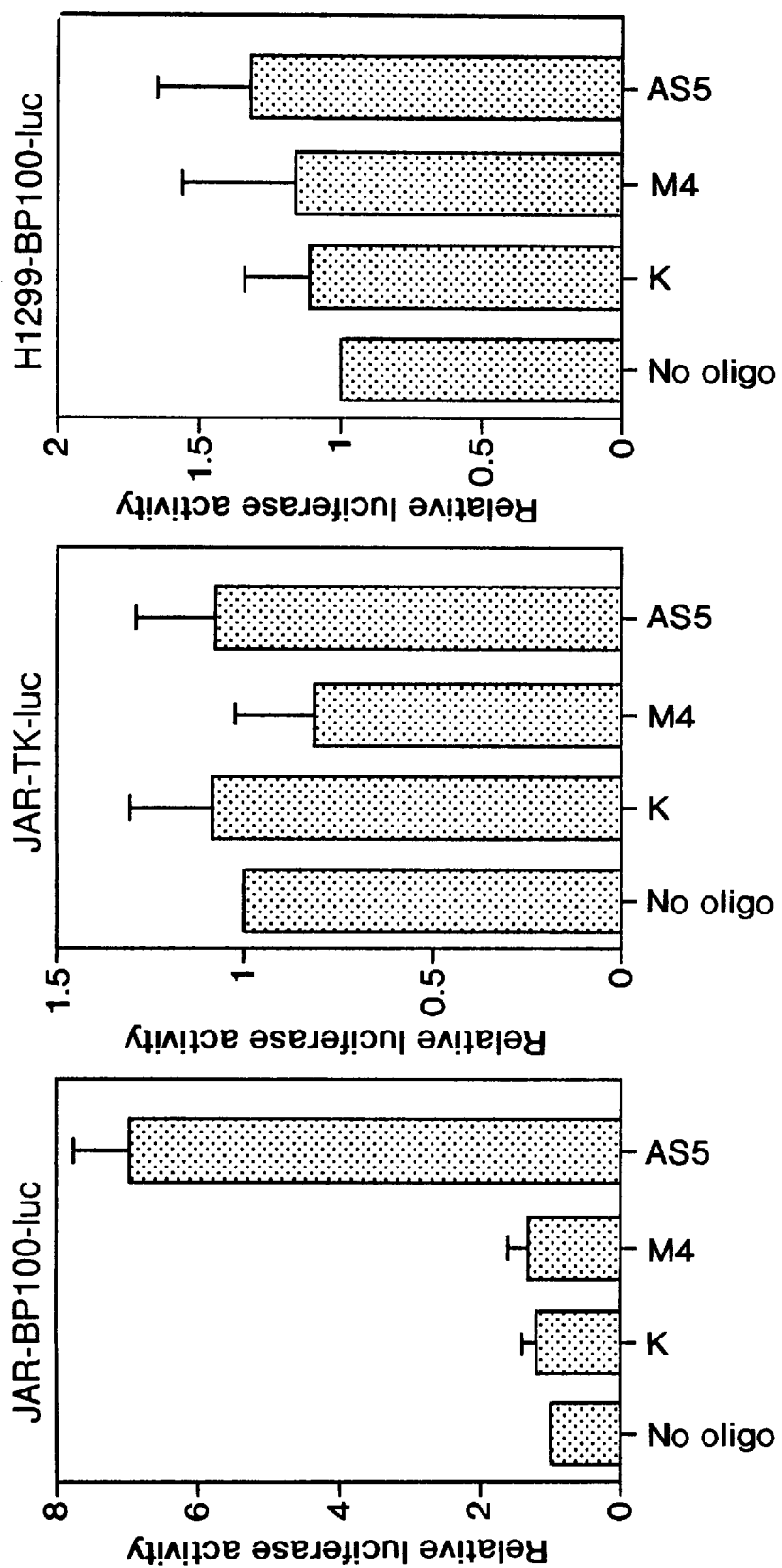

353-TCCATGTAGACACTCACTCTTGTCCACAGTGGAACTTCCACCCTCACTAGTTTCCTGGAACATGTTCTCGAA-425 SEQ ID NO: 49
SEQ ID NO.: 35   AS5-1: TGTAGACACTCACTCTTGTC   AS5: GGAACTTCCACCCTCACTAG SEQ ID NO.: 28
  SEQ ID NO.: 36  AS5-2: CACTCACTCTTGTCCACAGT   AS5-5: ACCCTCACTAGTTTTCCTGG SEQ ID NO.: 39
  SEQ ID NO.: 37  AS5-3: ACTCTTGTCCACAGTGGAAC   AS5-6: CACTAGTTTTCCTGGAACAT SEQ ID NO.: 40
  SEQ ID NO.: 38  AS5-4: TGTCCACAGTGGAACTTCCA   AS5-7: TTCCTGGAACATGTTCTCGA SEQ ID NO.: 41

FIG. 9A

FIG. 10A-1  FIG. 10A-2
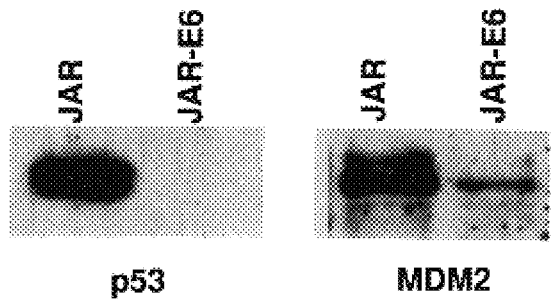
p53  MDM2
FIG. 10B-1  FIG. 10B-2
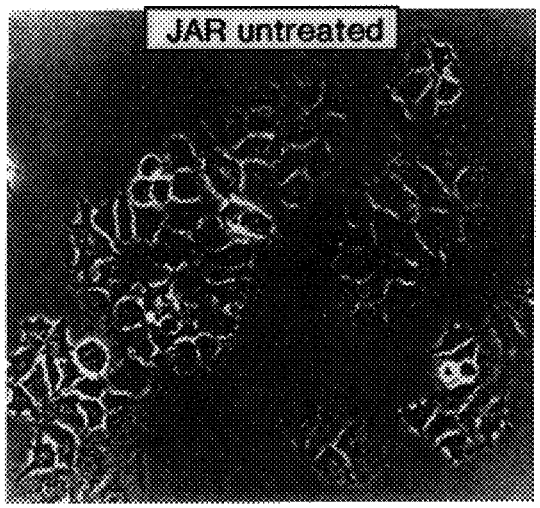 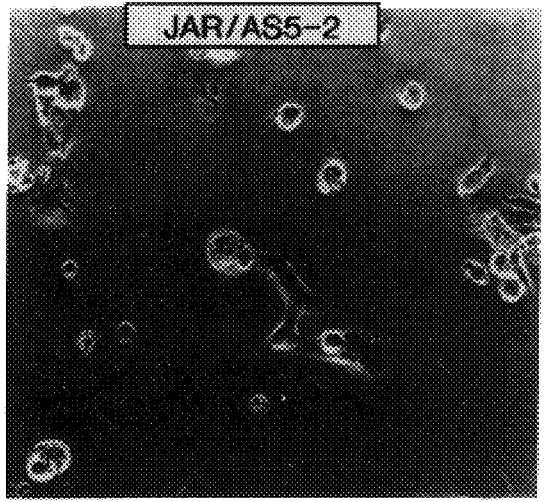
FIG. 10B-3  FIG. 10B-4
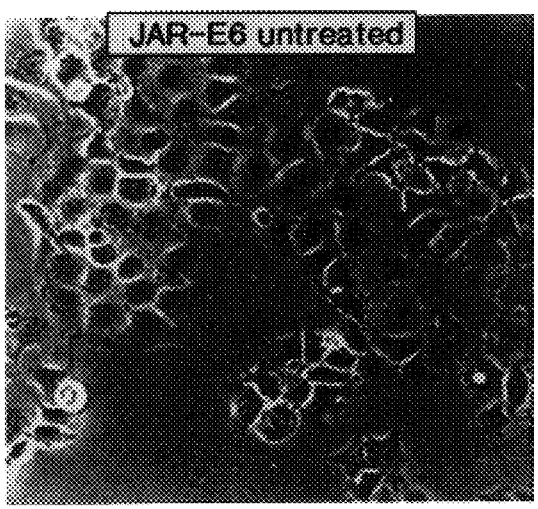 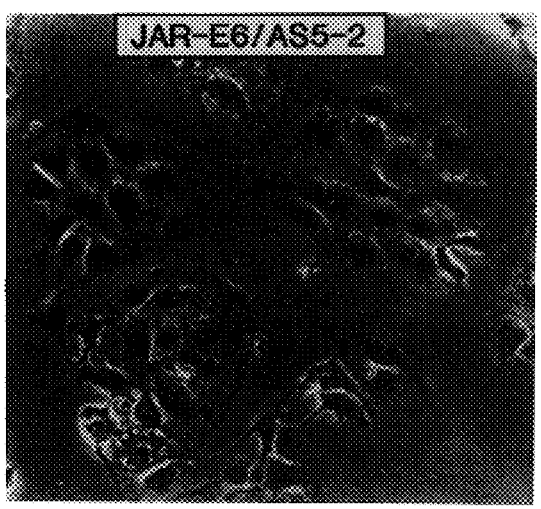

Control treated      AS5-2 treated
MCF-7
Breast tumor
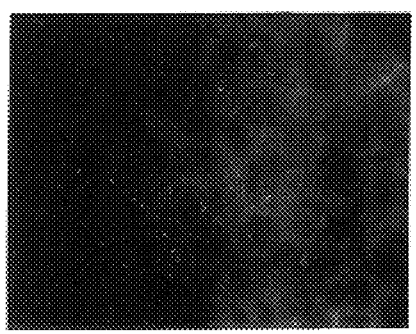 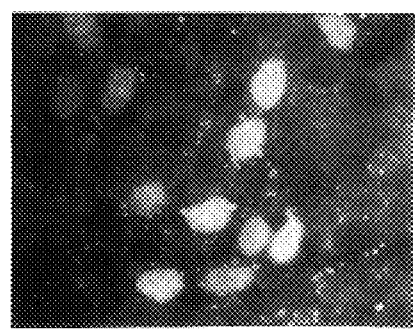
FIG. 11A      FIG. 11B
SK-N-SH
Neuroblastoma
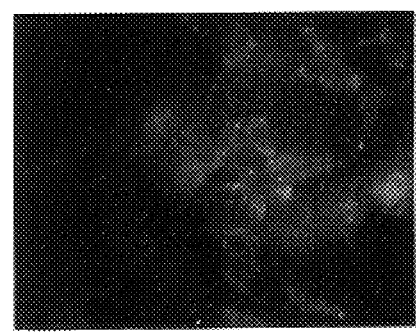 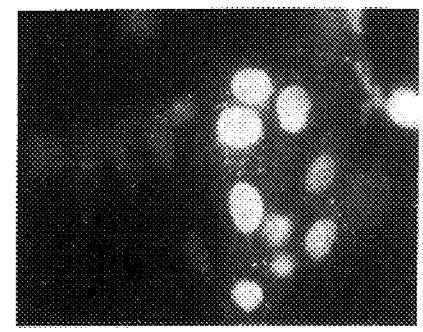
FIG. 11C      FIG. 11D
A172
Glioblastoma
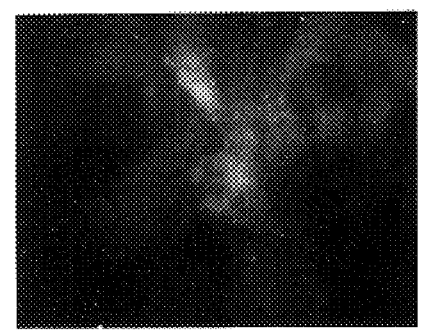 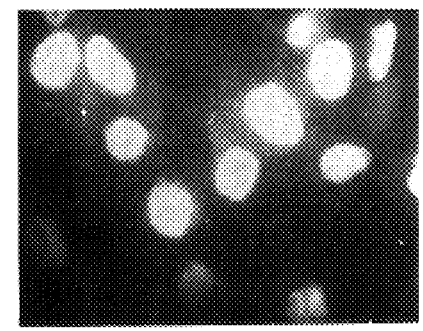
FIG. 11E      FIG. 11F
HT1080
Fibrosarcoma
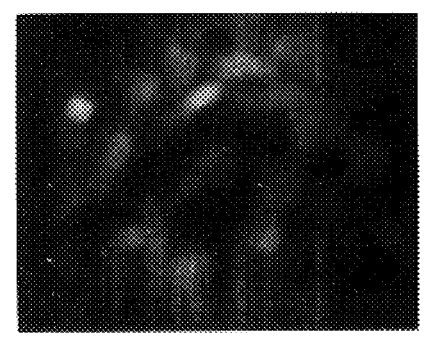 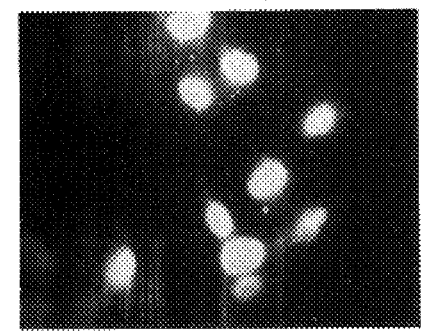
FIG. 11G      FIG. 11H FIG. 14A
Control treated
FIG. 14B
AS5-2 treated
HT1080
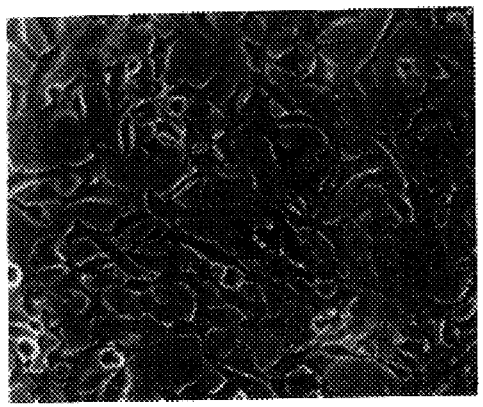
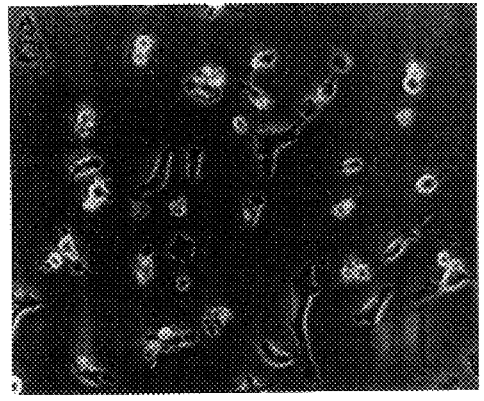
PA-1
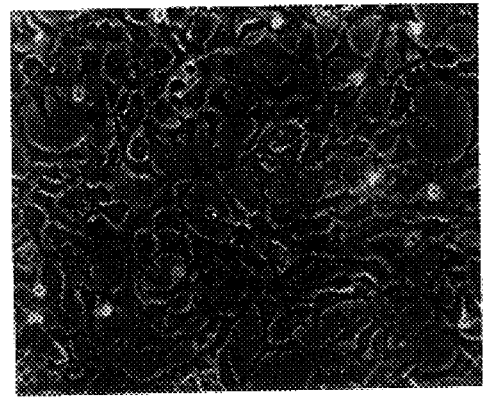
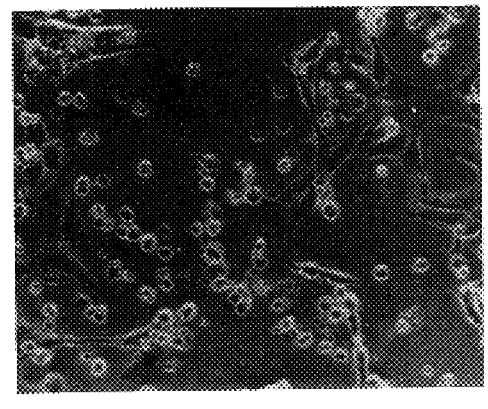
FIG. 14C
FIG. 14D

MDM2-SPECIFIC ANTISENSE OLIGONUCLEOTIDES

This is a continuation-in-part of U.S. application Ser. No. 08/916,384, filed Aug. 22, 1997.

BACKGROUND OF THE INVENTION

1. Field of the Invention

The invention relates to modulation of gene expression. In particular, the invention relates to modulation of gene expression through an antisense approach.

2. Summary of the Related Art

Regulation of gene expression is a complex process, and many aspects of this process remain to be understood. Aberrant gene expression appears to be responsible for a wide variety of inherited genetic disorders, and has also been implicated in numerous disease states including pathological conditions stemming from tumorigenic growth. A great deal of cancer related research pertains to the elucidation of the roles and interaction of tumor suppressor genes and oncogenes.

Several tumor suppressors have been identified. Marshall et al., Cell 64:313–326 (1991) teach that the WT1 gene was among the first tumor suppressors to be identified and isolated. Coopers et al., Cancer Invest. 12(1):57–65 (1994) disclose that the WT1 gene product is a protein with four zinc fingers suspected to be a transcription factor. Anderson and Spandidos Onco-Suppresso (1990) disclose the NF1 gene, another tumor suppressor, involved in the development of neurofibromatosis functioning as a GTPase-activating protein for the GTP-binding protein $p21^{ras}$. In addition, Sager et al., Science 246:1406–1412 (1989) disclose several genes involved in the development of colon cancer, namely DCC, MCC and APC (FAP) suggesting that their products might also perform tumor suppressor functions.

To date however, the best characterized tumor suppressors are the RB and the p53 gene products.

Levine, Bioessays 12(2):60–66 (1990) teaches RB gene inactivation in retinoblastoma. Notably, Levine et al., Nature 351:453–456 (1991), Weinberg et al., Neur. 11:191–196 (1991), and Williams et al., Nature Genet. 7:480–484 (1994), teach RB gene inactivation in many other tumor types including breast tumors, bladder carcinoma, and lung tumors.

Levine et al., Nature 351:453–456 (1991) have disclosed that the p53 tumor suppressor gene encodes a phosphoprotein suspected to play a pivotal role in fundamental biological processes in cell proliferation and differentiation). Lane, Br. Med. Bull. 50:(3)582–599 (1994) also teaches the p53 gene involvement in various types of tumors. In addition, Lowe et al., Cell 74:957–967 (1993); see also Lowe et al., Science 266:807–810 (1994); Kastan et al., Cancer Res. 51:6304–6311 (1991); Fritsche et al., Oncogene 8:307–318 (1993) disclose that p53 activation is an important factor in mediating the cytotoxic effects of many cancer treatments, including chemotherapy and radiation, and that p53 is required to trigger apoptosis in response to chemotherapy.

Further elucidation of the role of both RB and p53 regulation has led to the mouse double-minute, or mdm2 oncogene. The human cDNA sequence (SEQ ID NO: 1) is disclosed in Volgelstein and Kinzler (U.S. Pat. No. 5,411,860) and the mouse cDNA sequence (SEQ ID NO: 12) can be found in GenBank, Accession No. U40145. Cahill-Snyder et al., Somatic Cell. Mol. Genet. 13:235–244 (1987) teach the identification of this oncogene because of its overexpression in a spontaneously transformed tumor cell line. Fakharzadeh et al., EMBO J. 10:1565–1569 (1991) disclose the ability of the mdm2 gene to augment tumorigenesis in NIH3T3 cells and Rat2 cells when overexpressed. More recent studies teach that mdm2 gene amplification and its subsequent overexpression occur frequently in a variety of tumors including soft tissue sarcomas, osteosarcomas, leukemias and gliomas Cordon-Cardo et al., Cancer Res. 54:794–799 (1994); Ladanyi et al., Cancer Res. 53:16–18 (1993); Leach et al., Cancer Res. 53:2231–2234; (1993); Oliner et al., Nature 358:80–83 (1992); Reifenberger et al., Cancer Res. 53:2736–2739 (1993); Sheikh et al. Cancer Res. 53:3226–3228 (1993); Matsumura et al., Oncology 53:308–312 (1996); Bueso-Ramos et al., Blood 82:2617–2623 (1993); Watanake et al., Blood 84:3158–3165 (1994).

Recently, investigators have sought to elucidate the mechanisms responsible for mdm2 putative oncogenicity and its interactions with tumor suppressors. Xiao et al., Nature 375:694–698 (1995) teach that the oncogenic activity of mdm2 is due, at least in part, to its ability to bind and inhibit p53 and RB transcriptional activation. Chen et al., Mol. Cell. Biol. 13:(7)4107–4114 (1993) have disclosed that p53 inactivation is due to the formation of a tight complex between the amino terminus of MDM2 and the amino terminal transactivation domain of p53. Chen et al., Mol. Cell. Biol. 16:2445–2452 (1996) has also disclosed that MDM2 inhibits $G_1$ arrest and the apoptotic functions of p53. In addition, Wu et al., Genes Dev. 7:1126–1132 (1993) disclose that mdm2 is transcriptionally activated by p53, thus forming an autoregulatory negative feedback loop.

The MDM2 protein has also been shown to interact with other tumor suppressors and other molecules. Xiao et al. (supra) Martin et al., Nature 375:691–694 (1995) have recently disclosed the involvement of the same domain in the amino terminus of the MDM2 protein in the transcriptional activation of E2F1 DP1 further speculating a synergistic stimulation of the transcriptional activity of E2F1DP1 by relieving the negative control of RB on E2F1.

The significance of MDM2 in cell regulatory functions has recently been extended to other interactions. Marechal et al., Mol. Cell. Biol. 14:7417–7429 (1994) teach that the MDM2 protein binds to the ribosomal protein L5-5S RNA complex while Elenbaas et al., Mol. Med. 2:(4)439–451 (1996) teach MDM2 interaction with specific RNA structures.

From the available literature, it is clear that efforts should be directed to identify modulators and potentiators of tumor suppressor genes expression as a possible therapeutic approach to tumorigenesis. The identification of regulatory proteins acting on tumor suppressors could potentially lead to the development of therapeutic approaches to tumorigenesis by the activation of tumor suppressor functions. Thus, there is a need for the identification of tumor suppressor regulators and of methods to activate tumor suppressors in the context of chemotherapy. In this context, there is a need to elucidate the mechanism(s) involved in the development of resistance to chemotherapy in tumor cells. There is therefore, a need to develop better tools to carry out such investigations. Ideally, such tools should take the form of improved antisense oligonucleotides that inhibit mdm2. Kondo et al., Oncogene 10:(10)2001–2006 (1995) has disclosed that antisense oligonucleotide phosphodiesters directed against mdm2 increase the susceptibility of tumor cells to cisplatin-induced apoptosis. Kondo et al. have recently disclosed that mdm2 gene induced the expression of the multidrug resistance gene (mdr1) and that of its product P-glycoprotein (P-gp) conferring resistance to the apoptopic cell death induced by DNA-damage inducing drugs. Kondo et al., Br. J. Cancer 74:(8)1263–1268 (1996) teach the antisense inhibition of the mdm2 gene to inhibit expression of p-gp in mdm2 expressing glioblastoma cells further suggesting that the mdm2 gene may play an important role in the development of MDR phenotype in human tumors. Unfortunately the oligonucleotides disclosed are phosphodiester oligonucleotides and thus not suitable as investigative tools for the purposes discussed herein, and as potential therapeutics for the treatment of neoplastic diseases. Therefore, there remains a need for improved antisense oligonucleotides. Such improved antisense oligonucleotides should preferably also represent potential therapeutics for the treatment of neoplastic disease.

BRIEF SUMMARY OF THE INVENTION

The invention relates to modulation of gene expression. In particular, the invention relates to modulation of gene expression through an antisense approach. The invention provides better tools to identify modulators and potentiators of tumor suppressor gene expression as a possible therapeutic approach to tumorigenesis, and to elucidate the mechanism(s) involved in the development of resistance to chemotherapy in tumor cells. In particular the invention provides improved antisense oligonucleotides complementary to a portion of the MDM2-encoding RNA and methods for using such antisense oligonucleotides as analytical and diagnostic tools, as potentiators of transgenic animal studies and for gene therapy approaches, and as therapeutic agents. The invention further provides methods to activate tumor suppressors. In addition, the invention also provides methods to augment and synergistically activate tumor suppressors in conjunction with the use of a DNA-damage inducing agent.

In a first aspect, the invention provides improved antisense oligonuclcotides that inhibit the expression of the MDM2 protein. Such antisense oligonucleotides are complementary to a portion of MDM2-encoding RNA. Preferably, such antisense oligonucleotides contain one or a plurality of internucleoside linkages and optionally contain either deoxyribonucleosides, ribonucleosides, 2'-O-substituted ribonucleosides (preferably 2'-O-methyl ribonucleotides), or any combination thereof. Particularly preferred antisense oligonucleotides according to this aspect of the invention include chimeric oligonucleotides and hybrid oligonucleotides.

In a second aspect, the invention provides methods for activating a tumor suppressor in a cell, including providing to a cell expressing the mdm2 gene an antisense oligonucleotide according to the invention. In a preferred embodiment of this aspect, the invention provides a method for activating p53 tumor suppressor in a cell. In a particularly preferred embodiment, the present invention provides a method for synergistically enhancing DNA-damage induced activation of p53 in tumor cells by contacting tumor cells with both a DNA-damage inducing agent and an antisense oligonucleotide according to the invention.

In a third aspect, the invention provides a method for inhibiting tumor growth in a mammal, including a human, comprising administering to the mammal, which has at least one mdm2-expressing tumor cell present in its body, a therapeutically effective amount of an antisense oligonucleotide according to the invention for a therapeutically effective period of time. In a preferred embodiment of this aspect, the method comprises co-administration of a DNA-damage inducing agent.

In a fourth aspect, the invention provides a method for investigating the role of the MDM2 oncoprotein in tumorigenic growth. In the method according to this aspect of the invention, the cell type of interest is contacted with an antisense oligonucleotide according to the invention, resulting in inhibition of expression of the mdm2 oncogene in the cell. The antisense oligonucleotides can be administered at different points in the cell cycle, or in conjunction with promoters or inhibitors of cell growth to determine the role of the MDM2 protein in the growth of the tumor of interest.

BRIEF DESCRIPTION OF THE DRAWINGS

FIG. 1A, shows the nucleotide sequence of the mdm2 human cDNA comprising the nucleotide acid sequences set forth in the Sequence Listings as SEQ ID NO:1; FIG. 1B, shows the nucleotide sequence of the murine mdm2 mRNA comprising the nucleotide acid sequences set forth in the Sequence Listings as SEQ ID NO:12.

FIGS. 3A–C are graphic representations showing the activation of the p53-responsive luciferase reporter expression by representative, nonlimiting, synthetic antisense oligonucleotides according to the present invention.

FIG. 9A displays the sequence of the anti-mdm2 antisense phosphorothioate oligonucleotides. All sequences are displayed 3' to 5'. The top sequence represents the non-coding strand of human mdm2.

LC: control with lipofection alone.

FIG. 10–1 and –2 display the induction of apoptosis by HDMAS5-2, which is shown to be p53-dependent. JAR cells stably transfected with an actin promoter-driven HPV E6 construct (JAR-E6) expressed no detectable p53 and significantly reduced level of MDM2 in Western blot analyses. Identical amounts of total protein were loaded on each lane. FIGS. 10B–1 to –4 display cells (treated and untreated) with oligonucleotide AS5-2 and demonstrates that JAR-E6 cells are resistant to apoptosis induction by AS5-2. JAR and JAR-E6 cells were treated with 200 nM of AS5-2 for 24 hr. HDMAS5-2 induced significant cell death in JAR cells, but not in JAR-E6 cells.

FIGS. 11A–H display induction of p53 accumulation by oligonucleotide AS5-2 in different tumor cell lines. Cells were cultured on chamber slides, treated with 200 nM HDMAS5-2 or control oligonucleotide K for 20 hr, and stained for p53 expression using Pab1801. Treatment with oligonucleotide AS5-2 induced strong nuclear p53 accumulation in cells with low basal levels of wild type p53.

FIG. 12A shows that inhibition of mdm2 expression results in an increase of p53 level. Cells were treated with 200 nM of AS5-2 or control oligonucleotide K for 20 hr. p53 protein levels were detected by Western blot with antibody DO-1. Identical amounts of total protein were loaded on each lane. The double band in MCF-7 is due to a p53 polymorphic allele.

FIGS. 14A–D show the induction of cell death by inhibition of mdm2 expression. Cells were treated with 200 nM AS5-2 or control oligonucleotide K for 24 hr and photographed. Examples of cell lines undergoing significant cell death characteristic of apoptosis are shown.

DETAILED DESCRIPTION OF THE PREFERRED EMBODIMENTS

Figure 2A:
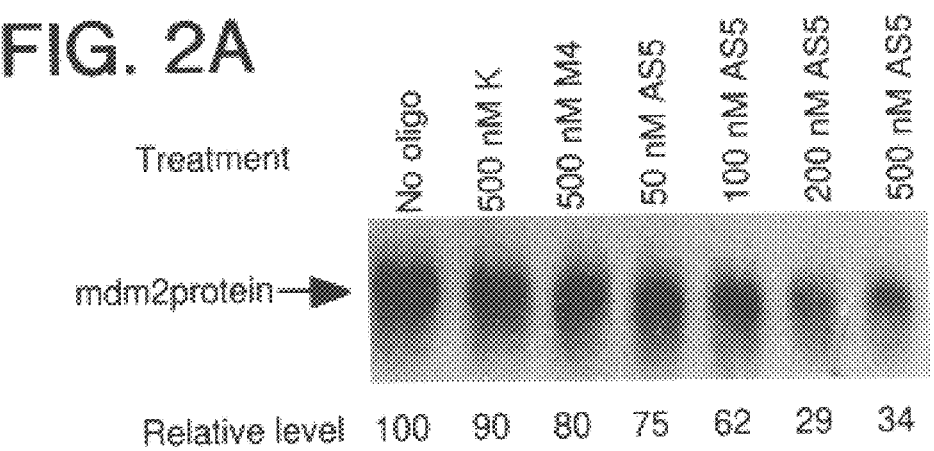
FIG. 2A is a representation of a Western blot showing the quantitation of MDM2 protein in cells treated with an antiscnse oligonucleotide according to the present invention; panel B is a representation of a Northern blot showing the quantitation of mdm2 mRNA in cells treated with an oligonucleotide according to the present invention; panel C is a representation of a Western blot showing the quantitation of p21/WAF protein in cells treated with an oligonucleotide of the invention.

The invention relates to modulation of gene expression. In particular, the invention relates to modulation of gene expression of oncogenes. More specifically, the invention relates to the modulation of tumor suppressor activity. The invention provides methods to activate tumor suppressors. The invention provides improved antisense oligonucleotides complementary to a portion of the MDM2-encoding RNA and methods for using such antisense oligonucleotides as analytical and diagnostic tools, as potentiators of transgenic animal studies and for gene therapy approaches, and as potential therapeutic agents. The invention further provides methods to activate tumor suppressors. The invention also provides methods to augment and synergistically activate a tumor suppressor in conjunction with the use of a DNA-damage inducing agent. The patents and publications identified in this specification are within the knowledge of those skilled in this field and are hereby incorporated by reference in their entirety.

In a first aspect, the invention provides improved antisense oligonucleotides that inhibit the expression of the mdm2 gene. Such antisense oligonucleotides are preferably complementary to a portion of MDM2-encoding RNA shown in FIG. 1 (SEQ ID NO:1). Preferably, such antisense oligonucleotides contain one or more modified internucleoside linkages and may optionally contain either deoxyribonucleosides, ribonucleosides or 2'-O-substituted ribonucleosides, or any combination thereof. Particularly preferred antisense oligonucleotides according to this aspect of the invention include chimeric oligonucleotides and hybrid oligonucleotides.

For purposes of the invention, "complementary" means being sufficiently complementary to have the ability to hybridize to a genomic region, a gene, or an RNA transcript thereof under physiological conditions. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization. As a practical matter, such complementarity can be inferred for example from the observation of specific mdm2 expression inhibition.

Particularly preferred improved oligonucleotides according to the invention are complementary to all or a portion of a region of MDM2-encoding RNA that consists of a nucleotide sequence selected from the group of sequences in the Sequence Listing as SEQ ID NOS:2–4, 7–11, and 13–24 (see Table 1, which also displays the corresponding antisense sequences). Preferably such improved oligonucleotides are complementary to a sequence that overlaps one of such sequences by at least one nucleotide. Preferably such improved antisense oligonucleotides according to this embodiment of the invention have nucleotide sequences of from about 12 to about 50 nucleotides. Most preferably, oligonucleotides have nucleotide sequences of from about 13 to about 19 nucleotides.

other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages. In certain preferred embodiments, these internucleoside linkages may be phosphodiester, phosphotriester, phosphorothioate, or phosphoramidate linkages, or combinations thereof. The term oligonucleotide also encompasses

TABLE 1

| NAME* | SEQ. ID NO. | SEQUENCE | TARGET MAP-SITE† |
|---|---|---|---|
| S4    | 2  | 5'-TTG GCC AGT ATA TTA TGA CT-3'  | 481–500 |
| AS4   | 27 | 5'-AGT CAT AAT ATA CTG GCC AA-3'  | |
| S5    | 3  | 5'-CCT TGA AGG TGG GAG TGA TC-3'  | 695–714 |
| AS5   | 28 | 5'-GAT CAC TCC CAC CTT CAA GG-3'  | |
| S7    | 4  | 5'-TGG ATC AGG ATT CAG TTT CA-3'  | 1018–1037 |
| AS7   | 29 | 5'-TGA AAC TGA ATC CTG ATC CA-3'  | |
| S1    | 7  | 5'-ACC TCA CAG ATT CCA GCT TC-3'  | 357–376 |
| AS1   | 30 | 5'-GAA GCT GGA ATC TGT GAG GT-3'  | |
| S2    | 8  | 5'-CCA GCT TCG AAC AAG AGA AC-3'  | 369–388 |
| AS2   | 31 | 5'-GTC TCT TGT TCC GAA GCT GG-3'  | |
| S3    | 9  | 5'-TCT ACC TCA TCT AGA AGG AG-3'  | 780–799 |
| AS3   | 32 | 5'-CTC CTT CTA GAT GAG GTA GA-3'  | |
| S6    | 10 | 5'-TCC TTA GCT GAC TAT TGG AA-3'  | 1203–1222 |
| AS6   | 33 | 5'-TTC CAA TAG TCA GCT AAG GA-3'  | |
| S8    | 11 | 5'-TCA TGC AAT GAA ATG AAT CC-3'  | 1230–1249 |
| AS8   | 34 | 5'-GGA TTC ATT TCA TTG CAT GA-3'  | |
| S5-1  | 13 | 5'-ACA TCT GTG AGT GAG AAC AG-3'  | 669–688 |
| AS5-1 | 35 | 5'-CTG TTC TCA CTC ACA GAT GT-3'  | |
| S5-2  | 14 | 5'-GTG AGT GAG AAC AGG TGT CA-3'  | 675–694 |
| AS5-2 | 36 | 5'-TGA CAC CTG TTC TCA CTC AC-3'  | |
| S5-3  | 15 | 5'-TGA GAA CAG GTG TCA CCT TG-3'  | 680–699 |
| AS5-3 | 37 | 5'-CAA GGT GAC ACC TGT TCT CA-3'  | |
| S5-4  | 16 | 5'-ACA GGT GTC ACC TTG AAG GT-3'  | 685–704 |
| AS5-4 | 38 | 5'-ACC TTC AAG GTG ACA CCT GT-3'  | |
| S5-5  | 17 | 5'-TGG GAG TGA TCA AAA GGA CC-3'  | 704–723 |
| AS5-5 | 39 | 5'-GGT CCT TTT GAT CAC TCC CA-3'  | |
| S5-6  | 18 | 5'-GTG ATC AAA AGG ACC TTG TA-3'  | 709–728 |
| AS5-6 | 40 | 5'-TAC AAG GTC CTT TTG ATC AC-3'  | |
| S5-7  | 19 | 5'-AAG GAC CTT GTA CAA GAG CT-3'  | 717–736 |
| AS5-7 | 41 | 5'-AGC TCT TGT ACA AGG TCC TT-3'  | |
| S7-1  | 20 | 5'-TGA ACA TTC AGG TGA TTG GT-3'  | 998–1017 |
| AS7-1 | 42 | 5'-ACC AAT CAC CTG AAT GTT CA-3'  | |
| S7-2  | 21 | 5'-ATT CAG GTG ATT GGT TGG AT-3'  | 1003–1022 |
| AS7-2 | 43 | 5'-ATC CAA CCA ATC ACC TGA AT-3'  | |
| S7-3  | 22 | 5'-AGG TGA TTG GTT GGA TCA GGA-3' | 1007–1027 |
| AS7-3 | 44 | 5'-TCC TGA TCC AAC CAA TCA CCT-3' | |
| S7-4  | 23 | 5'-ATT CAG TTT CAG ATC AGT TT-3'  | 1027–1046 |
| AS7-4 | 45 | 5'-AAA CTG ATC TGA AAC TGA AT-3'  | |
| S7-5  | 24 | 5'-GAT CAG TTT AGT GTA GAA TT-3'  | 1038–1057 |
| AS7-5 | 46 | 5'-AAT TCT ACA CTA AAC TGA TC-3'  | |

*As used herein, sequences whose names begin with "S" are in the sense orientation, and sequences whose names begin with "AS" are in the antisense orientation. Furthermore, an "S" sequence and an "AS" sequence whose names have the same number designation are complementary in the Watson-Crick sense. For example, the sequence AS2 is complementary to S2:
5'-CCA GCT TCG AAC AAG AGA AC-3' (SEQ ID NO: 8)
••• ••• ••• ••• ••• ••
3'-GGT CGA AGC CTT GTT CTC TG-5' (SEQ ID NO: 31)
†Numbering is according to SEQ ID NO: 1 in the Sequence Listing.

For purposes of the invention, the term "oligonucleotide" includes polymers of two or more deoxyribonucleosides, ribonucleosides, or 2'-O-substituted ribonucleoside residues, or any combination thereof. Preferably, such oligonucleotides have from about 8 to about 50 nucleoside residues, and most preferably from about 12 to about 30 nucleoside residues. The nucleoside residues may be coupled to each such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an -O-lower alkyl group containing 1–6 saturated or unsaturated carbon atoms, or with an -O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group. 2' substitution may be with a hydroxy group (to produce a ribonucleoside), an amino or a halo group, but not with a 2'-H group.

Particularly preferred antisense oligonucleotides according to this aspect of the invention include chimeric oligonucleotides and hybrid oligonucleotides.

For purposes of the invention, a "chimeric oligonucleotide" refers to an oligonucleotide having more than one type of internucleoside linkage. One preferred embodiment of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region. Preferably, such chimeric oligonucleotides contain at least three consecutive internucleoside linkages selected from phosphodiester and phosphorothioate linkages, or combinations thereof For example, U.S. Pat. No. 5,149,797 describes traditional chimeric oligonucleotides having a phosphorothioate core region interposed between methylphosphonate or phosphoramidate flanking regions. U.S. patent application Ser. No. 08/516, 454, filed on Aug. 9, 1995 discloses "inverted" chimeric oligonucleotides comprising one or more nonionic oligonucleotide region (e.g. alkylphosphonate and/or phosphoramidate and/or phosphotriester internucleoside linkage) flanked by one or more region of oligonucleotide phosphorothioate.

For purposes of the invention, a "hybrid oligonucleotide" refers to an oligonucleotide having more than one type of nucleoside. One preferred embodiment of such a hybrid oligonucleotide comprises a ribonucleotide or 2'-O-substituted ribonucleotide region, preferably comprising from about 2 to about 12 2'-O-substituted nucleotides, and a deoxyribonucleotide region. Preferably, such a hybrid oligonucleotide will contain at least three consecutive deoxyribonucleosides and will also contain ribonucleosides, 2'-O-substituted ribonucleosides, or combinations thereof Examples of such hybrid oligonucleotides are disclosed in U.S. Pat. Nos. 5,652,355 and 5,652,356.

Improved antisense oligonucleotides according to the invention have improved ability to inhibit mdm2 expression relative to prior art oligonucleotides. The exact nucleotide sequence and chemical structure of an antisense oligonucleotide according to the invention can be varied within the parameters described herein, so long as the oligonucleotide retains its improved ability to inhibit mdm2 expression. This is readily determined by testing whether the particular antisense oligonucleotide is active by determining steady state levels of MDM2 protein, by determining the amount of MDM2 co-precipitated with p53, by assaying p53-inducible gene expression, by assaying p53 transcriptional activity, by analyzing total genomic DNA size, or by observing cell morphologies characteristic of apoptosis, all of which are described in detail in this specification.

Antisense oligonucleotides according to the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG). (See, e.g., Pon (1993) Methods in Molec. Biol. 20:465).

Antisense oligonucleotides according to the invention are useful for a variety of purposes. For example, they can be used as "probes" of the physiological function of MDM2 by being used to inhibit the activity of MDM2 in an experimental cell culture or animal system and to evaluate the effect of inhibiting such MDM2 activity. This is accomplished by administering to a cell or an animal an antisense oligonucleotide according to the invention and observing any phenotypic effects. In this use, antisense oligonucleotides according to the invention are preferable to traditional "gene knockout" approaches because they are easier to use and can be used to inhibit MDM2 activity at selected stages of tumor development or differentiation. Thus, antisense oligonucleotides according to the invention can serve as probes to test the role of MDM2 in various stages of tumorigenesis.

Finally, antisense oligonucleotides according to the invention are useful in therapeutic approaches to benign and malignant tumors and other human diseases involving altered patterns of gene expression.

Antisense oligonucleotides according to the invention are useful for benign and malignant tumors to inhibit mdm2 expression to reactivate or enhance tumor suppressors such as p53 in tumors, and to enhance the p53-stimulatory effect of DNA-damage. In addition, several types of tumors (e.g., osteosarcomas, gliomas, and breast cancer) have been found to overexpress mdm2. Antisense inhibition of mdm2 in these tumors reactivates p53 and reduces other p53-independent oncogenic activities of mdm2. Furthermore, the antisense oligonucleotides according to the invention are useful in the treatment of tumors that contain wild-type p53 to augment the effects of DNA-damaging based therapies. The antitumor utility of antisense oligonucleotides according to the invention is described in detail in the following paragraphs.

The present invention is also useful in enhancing gene therapy involving the introduction of p53 into p53-mutant tumors by inhibiting the MDM2-negative feed back loop.

For therapeutic use, antisense oligonucleotides according to the invention may optionally be formulated with any of the well known pharmaceutically acceptable carriers or diluents. This formulation may further contain one or more mdm2 inhibitor(s) and/or one or more additional mdm2 antisense oligonucleotide(s), or it may contain any other pharmacologically active agent, as discussed elsewhere in this specification.

In a second aspect, the invention provides methods for activating a tumor suppressor in a cell including contacting an antisense oligonucleotide according to the invention to a portion of MDM2-encoding RNA. In a preferred embodiment of this aspect, the invention provides a method for activating p53 tumor suppressor in a cell. In a particularly preferred embodiment, the present invention provides a method for synergistically enhancing DNA damage-induced activation of p53 by contacting tumor cells with a DNA-damage inducing agent and an antisense oligonucleotide according to the invention.

The term "tumor suppressor" is used to denote a gene involved in normal control of cellular growth and division which when inhibited contributes to tumor development. Representative examples of tumor suppressor genes include the RB gene isolated from a region deleted in retinoblastoma cells, the WT1 gene isolated from 11p3, which is occasionally deleted in Wilms' tumor types, the NF1 gene involved in neurofibromatosis, and the p53 gene, which has been found to be associated with a wide variety of tumors.

The term "p53" is used to designate the gene that encodes the nuclear phosphoprotein p53, which is involved in the regulation of fundamental biological processes in cell proliferation and cell death. This protein is also responsible for mediating cytotoxicity of anticancer therapy, and has been shown to act as a tumor-suppressor protein.

As used herein, the designation "DNA-damage inducing agent" is used to denote antineoplastic compounds that are capable of interfering with DNA synthesis at any stage of the cell cycle. As a practical matter, such activity can be inferred by the observation of cell apoptosis. Examples of such agents include but are not limited to alkylating agents (e.g., mechlorethamine, chlorambucil, cyclophosphamide, mephalan, or ifosfamide), S-phase specific antimetabolites (e.g., folate antagonists, purine antagonists, or cytarabine), plant alkaloids (e.g., vinblastine, vincristine, or podophyllotoxins), antibiotics (e.g., doxorubicin, bleomycin, or mitomycin), nitrosureas (e.g., carmustine, or lomustine), inorganic ions (such as cisplatin). Etoposide and cisplatin are other chemotherapy drugs that are known to activate p53 by causing DNA damage and are contemplated for use in the invention.

The third aspect of the invention sets forth a method for inhibiting tumor growth in a mammal, including a human, comprising administering to the mammal, which has at least one tumor cell present in its body, a therapeutically effective amount of an antisense oligonucleotide according to the invention for a therapeutically effective period of time. In the method according to this aspect of the invention a therapeutically effective amount of an antisense oligonucleotide according to the invention is administered for a therapeutically effective period of time to an animal, including a human, which has at least one tumor cell present in its body.

As used herein the term "tumor growth" is used to refer to the growth of a tumor cell. A "tumor cell" is a neoplastic cell. A tumor cell may be benign, i.e. one that does not form metastases and does not invade and destroy adjacent normal tissue, or malignant, i.e. one that invades surrounding tissues, is capable of producing metastases, may recur after attempted removal, and is likely to cause death of the host.

The terms "therapeutically effective amount" and "therapeutically effective period of time" are used to denote known treatments at dosages and for periods of time effective to reduce tumor cell growth. Preferably, such administration should be parenteral, oral, sublingual, transdermal, topical, intranasal or intrarectal. When administered systemically, the therapeutic composition is preferably administered at a sufficient dosage to attain a blood level of antisense oligonucleotide from about 0.01 $\mu$M to about 10 $\mu$M. For localized administration, much lower concentrations than this may be effective, and much higher concentrations may be tolerated. Preferably, a total dosage of mdm2 inhibitor will range from about 0.1 mg oligonucleotide per patient per day to about 200 mg oligonucleotide per kg body weight per day.

In a preferred embodiment of this aspect, the method also includes the administration of a DNA-damage inducing agent. According to another embodiment, one or more of the oligonucleotides of the invention may be administered to an animal. This aspect of the invention provides methods for inhibiting tumor growth comprising administering to an animal, including a human, more than one antisense oligonucleotide according to the invention either sequentially or simultaneously in a therapeutically effective amount and for a therapeutically effective period of time.

In a fourth aspect, the invention provides a method for investigating the role of the MDM2 oncoprotein in cell development and differentiation and in tumorigenic growth of cells that are overexpressing mdm2. In the method according to this aspect of the invention, the cell type of interest is contacted with an antisense oligonucleotide according to the invention, resulting in inhibition of expression of the mdm2 oncogene in the cell. The antisense oligonucleotides can be administered at different points in the cell cycle, in conjunction with promoters or inhibitors of cell growth, or with DNA replication inhibitors to determine the role of the MDM2 protein in the growth of the tumor of interest.

We demonstrate below that antisense inhibition of MDM2 expression activates p53 in tumor cells containing either low or high levels of MDM2. Importantly, inhibition of MDM2 expression in cells with low levels of p53 uniformly results in p53 accumulation and increase of p53 activity. This response occurred in nearly all of the tumor and non-transformed cells tested. The only exceptions were HPV-positive cells, which have an independent E6-mediated mechanism of p53 degradation. The accumulation of p53 is due to a prolonged half-live, therefore, MDM2 plays a general role in maintaining p53 at low levels through degradation.

Our observations suggest that MDM2 overexpression is not the only indicator for p53 being in a functionally suppressed state. In tumor cells with low levels of MDM2 (which usually correlate with low levels of wild-type p53), MDM2 is still an active inhibitor of p53 through degradation. It is thus possible that the levels of MDM2 and p53 change during tumor development, such as due to p53-independent induction of MDM2 expression. Shaulian, Oncogene 15, 2717–2725 (1997). Thus MDM2 may be a causative factor in tumor development even when it is not overexpressed. Alternatively, these tumors may have successfully evaded the surveillance mechanism that signals for p53 activation, leaving the MDM2 regulatory loop at a pre-malignant state which prevents p53 accumulation.

The ubiquitous role of MDM2 in regulating p53 turnover suggests that many signals (such as DNA damage, hypoxia, oncogene activation) that can lead to p53 stabilization may act through modulation of p53-MDM2 interaction or MDM2 function. It has been demonstrated that DNA damage activation of DNA-PK phosphorylates p53 and MDM2 and inhibits MDM2 binding. Mayo et al., *Cancer Res.* 57, 5013–5016 (1997); Shieh et al., *Cell* 91, 325–334 (1997). Whether other p53-inducing signals act through similar mechanisms remains to be tested.

Our observations suggest that MDM2 overexpression is not the only indicator for p53 being in a functionally suppressed state. In tumor cells with low levels of MDM2 (which usually correlate with low levels of wild-type p53), MDM2 is still an active inhibitor of p53 through degradation. It is thus possible that the levels of MDM2 and p53 change during tumor development, such as due to p53-independent induction of MDM2 expression. Shaulian, *Oncogene* 15, 2717–2725 (1997). Thus, MDM2 may be a causative factor in tumor development even when it is not overexpressed.

The results of this study suggest that MDM2 is a useful drug target in many tumor types, even when it is not a causative factor during tumor development. Many types of tumors with wide impact or high mortality rate, such as tumors of the breast, liver, prostate, and brain, have p53 mutation frequencies of 20–30%. Hollstein et al., *Nucleic Acids Res.* 22, 3551–3555 (1994). Results presented below (see Table 2 and related text) demonstrate that the AS5-2 oligonucleotide causes about 70–80% cell death in C33A cells, which have mutant p53 and high MDM2 levels, indicating that oligonucleotides according to the invention can have an effect in cells (and potentially tumors) without a functional p53. Therefore, inhibitors of MDM2 may be useful for the majority of such cases.

Furthermore, MDM2 may have p53-independent functions that contribute to tumor development, such as regulation of Rb and E2F/DP1 (Xiao et al., *Nature* 375, 694–698 (1995); and Martin et al., *Nature* 375, 691–694 (1995)), and possibly regulation of the p53 homolog p73. Kaghad et al, *Cell* 90, 809–819 (1997)). Inhibition of MDM2 expression will abolish these functions as well.

The following examples are intended to further illustrate certain preferred embodiments of the invention and are not limiting in nature. Those skilled in the art will appreciate that modifications and variations for the following can be made without exceeding either the spirit or scope of the invention.

EXAMPLES

Example 1

Inhibition of mdm2 Expression By AS5

Choriocarcinoma JAR cells (ATCC) containing wild-type p53 were grown in DMEM medium supplemented with 1% FBS according to standard cell culture techniques. Cells were then treated for 18 hours with growth medium containing 50, 100, 200, and 500 nM of antisense oligonucleotides AS4 (SEQ ID NO:27), AS5 (SEQ ID NO:28), AS1 (SEQ ID NO:30), AS2 (SEQ ID NO:31), AS3 (SEQ ID NO:32), AS6 (SEQ ID NO:33), AS8 (SEQ ID NO:34), AS7 (SEQ ID NO:29) (complementary to sequences S4, S5, S1, S2, S3, S6, S8, and S7, respectively, of MDM2-encoding RNA), with 500 nM of a control oligonucleotide K (5'-CAGAGCCTTCATCTTCCCAG-3'; SEQ ID NO:6) complementary to an ion channel, or with 500 nM of a mismatch control oligonucleotide M4 (5'-GATGACTCACACCATCATGG-3'; SEQ ID NO:5) containing four mismatches within the same portion of MDM2-encoding RNA, and 7 µg/ml Lipofectin (Gibco BRL).

Treated cells were then harvested and lysed in lysis buffer (50 mM Tris pH 8.0, 5 mM EDTA, 150 mM NaCl, 0.5% NP40). Total protein was then extracted according to standard methods (see e.g., Current Protocols in Molecular Biology, John Wiley & Sons Inc. (1995)). Two mgs of total protein were mixed with 100 µl hybridoma supernatant containing an anti-MDM2 monoclonal antibody 2A10 (Chen et al., Mol. Cell. Biol. 13:4107–4114 (1993)), and with 20 µl of packed protein A-Sepharose beads (Sigma, St. Louis, Mo.). Immunoprecipitates were obtained by incubation of the mix at 4° C. for 3–5 hours on a rotator. The beads were then washed with lysis buffer three times. Immunoprecipitates were then boiled in loading dye (0.3 M Tris-HCl pH 8.8, 0.2% SDS, 10% glycerol 28 mM 2-mercaptoethanol and 24 µg/ml brompohenol blue). Samples were fractionated by electrophoresis on an SDS polyacrylamide gel with a 5% stacking gel and a 10% separation gel. The gel was then transferred onto an Immobilon P membrane (Millipore, Bedford, Mass.). The membrane was then blocked with PBS/5% non-fat milk+1/500 polyclonal serum for 1 hr. The membrane was then washed with PBS/5% milk and $I^{125}$ protein A (0.2 µCi/ml) for 1.5 hours. The filter was then washed with PBS and 0.1% Tween20 and exposed to a phosphorimaging screen.

As shown in FIG. 2A, treatment with oligonucleotide AS5 resulted in approximately 3–5 fold inhibition of mdm2 expression at concentrations between I100 and 400 nM. This effect was not observed with an oligonucleotide targeted to an unrelated ion channel gene (oligonucleotide K) or an AS5 mismatch control oligonucleotide containing 4 base mismatches with the same target (oligonucleotide M4).

Example 2

Alteration of mdm2 RNA by AS5

JAR cells were treated with 200 nM of antisense oligonucleotide AS5 (SEQ ID NO:28) with no oligonucleotide, with 200 nM of control oligonueleotide M4 (SEQ ID NO:5). After 18 hours, the treated cells were harvested and RNA was purified and quantitated according to standard methods. (see e.g., Current Protocols in Molecular Biology, John Wiley & Sons Inc. (1995)). Twenty µg of total RNA were run on a 1% agarose denaturing gel. mdm2 mRNA was detected by hybridization using an EcoRI-NcoI fragment specific for the human mdm2 cDNA between nucleotides 310–1633. The filter was then stripped and reprobed with a 1.2 kb fragment, which is a full length human GAPDH cDNA to normalize values on the basis of loading variations, according to standard methods.

Figure 2B:
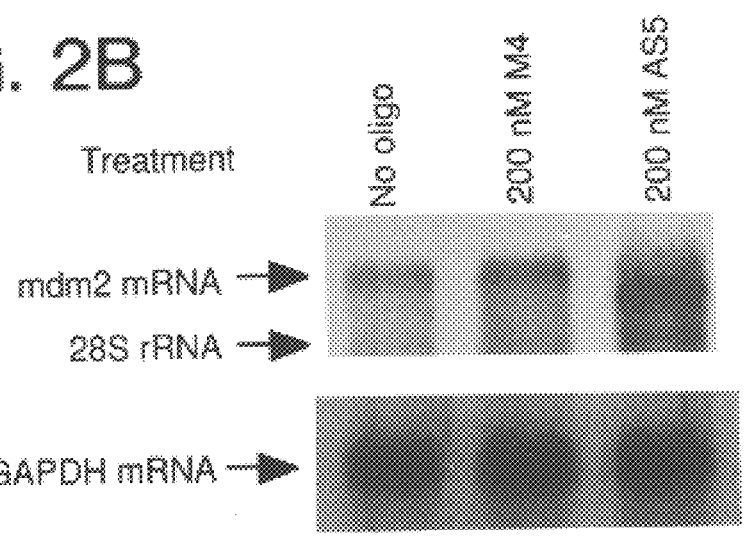

As shown in FIG. 2B, treatment with oligonucleotide AS5 (SEQ ID NO:28) resulted in a slight decrease in the molecular weight of the mdm2 mRNA band. This is consistent with RNase H cleavage at the site of the oligonucleotide AS5 hybridization (approximately 700 bp from the 5' end), which would reduce the molecular weight of the mRNA (normally approximately 5500 nt long) by approximately 12%. Most important, as shown in FIG. 2B, treatment with the AS5 resulted in 2.5 fold increase of mdm2 mRNA consistent with p53 activation in response to decreased MDM2 protein levels following inhibition of mdm2 expression. Comparable results were also obtained using osteosarcoma SJSA cells (ATCC) (data not shown).

Example 3

Induction of p21/WAF1 Expression by Oligonucleotide AS5

To assess the ability of the oligonucleotides of the invention to induce the expression of a p53-inducible gene, p21/WAF1 levels were examined in oligonueleotide-treated JAR cells. Total protein was purified from control oligonucleotide-treated cells and from antisense oligonucleotide-treated cells (200 nM oligonucleotide AS5) as described in Example 1. Equal amounts of purified total protein were immunoprecipitated and analyzed by Western blotting carried out for mdm2 detection using a polyclonal rabbit anti-human p21/WAF1 serum. Following hybridization, the blots were exposed to XAR film (Eastman Kodak, Rochester, N.Y.) and the autoradiograms are quantitated by phosphoroimaging.

Figure 2C:
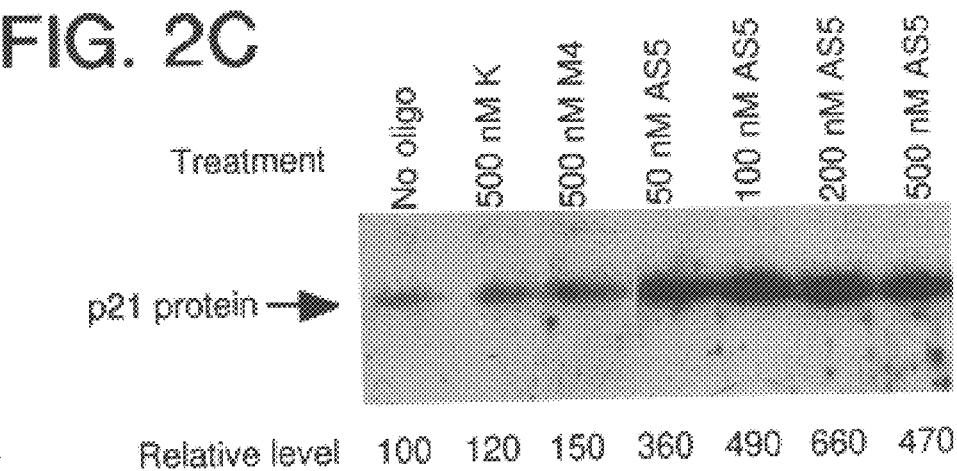

The results shown in FIG. 2C demonstrate a dose dependent induction of p21/WAF1 up to 6.6 fold (corresponding to 200 nM oligonucleotide) in antisense oligonucleotide-treated cells, relative to controls treated cells (lanes designated as No oligo, K and, M4).

Example 4

Activation of a p53-Responsive Reporter Gene by AS5

To measure p53 transcriptional activity in response to treatment with the oligonucleotides of the invention, a p53 responsive luciferase reporter BP100-luc, containing the p53 binding site from intron I of the mdm2 gene (Wu et al., J. Gene. Dev. 7:1126–1132 (1993), was transfected into JAR cells with a neomycin-resistant plasmid pCMV-neo-Bam (Baker et al., Science 249:912–915 (1990)), according to conventional methods (See e.g., *Molecular Cloning*, 2d Edition, Cold Spring Harbor Laboratory Press (1989)). Transfected cells were then plated and stable G418-resistant colonies were pooled and treated with no oligonucleotide, with 200 nM of control oligonucleotide M4 (SEQ ID NO:5), and with 200 nM of antisense oligonucleotide AS5 (SEQ ID NO:28). After 24 hours, luciferase activity levels in the oligonucleotide-treated cells were determined.

FIG. 3 shows the results obtained from at least four experiments for each data point. As shown in FIG. 3A, oligonucleotide AS5 activated the p53-responsive reporter expression by 7 fold. JAR cells stably transfected with a luciferase reporter driven by the thymidine kinase gene promoter (JAR-TK-luc) and H1299 cells containing no p53 that had been stably transfected with BP100-luciferase (H1299-BP1000-luc) were also tested. As shown in FIGS. 3B and 3C, oligonucleotide AS5 did not activate the reporter gene in these control experiments. Similar results were also observed using AS5 in osteosarcoma SJSA cells (data not shown).

Example 5

Reduction of p53-mdm2 Complex by the Antisense Oligonucleotides

Protein lysates from JAR cells treated with antisense oligonucleotides as described in Example 1 were immuno-precipitated with anti-p53 monoclonal antibody Pab421 (FIGS. 4A and 4B) (Harlow et al. J. Virol. 39:861–869 (1981)) or with polyclonal antibody 2A10 (panel C) according to the methods described in Example 1. The gel was then transferred onto an Immobilon P membrane (Millipore, Bedford, Mass.) to detect mdm2 co-precipitates.

Figure 4:
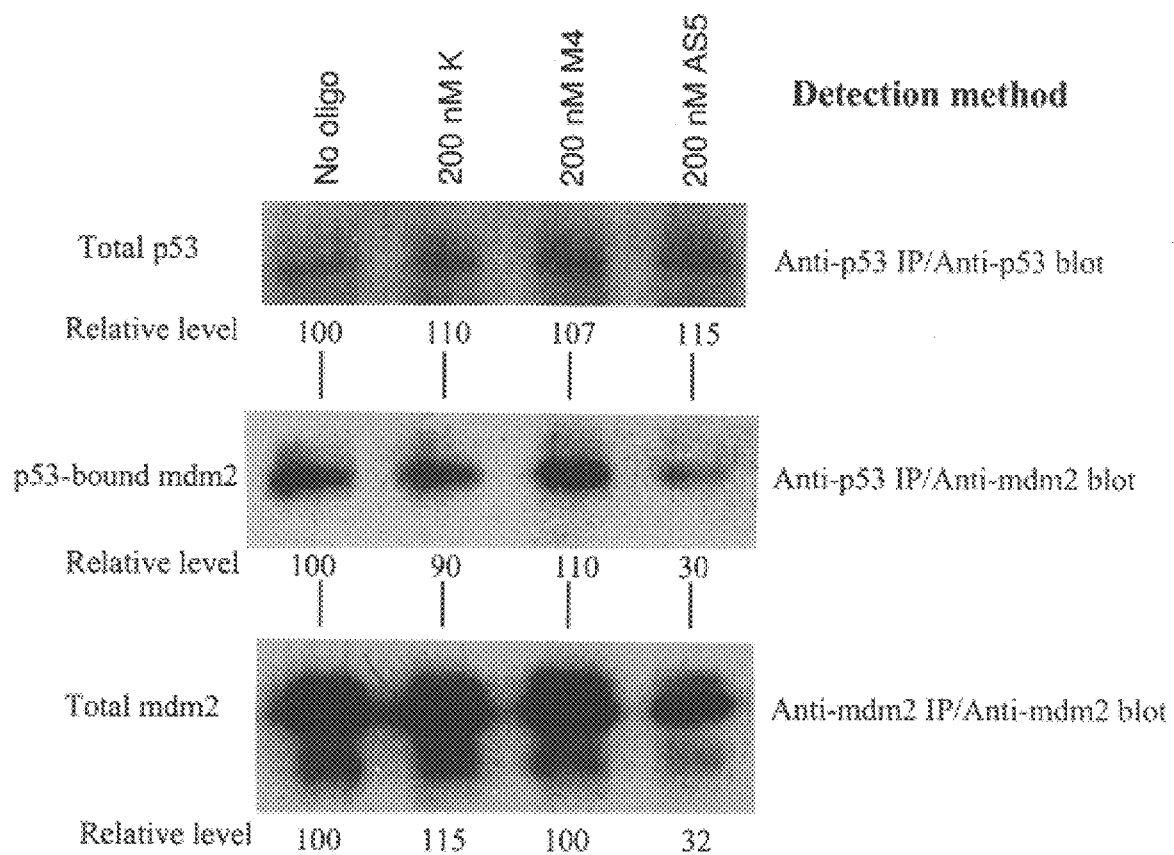
FIG. 4 is a representation of a Western blot showing the detection of total p53 protein (panel A), p53-bound MDM2 protein complex (panel B), and total MDM2 protein (panel C).

As shown in FIG. 4A, p53 levels did not change following treatment with oligonucleotide AS5. As shown in panel B, the amount of mdm2 co-precipitated with p53 were reduced by oligonucleotide AS5. The results demonstrated that a marked reduction in the mdm2-p53 complex is detected by Western blotting (see FIG. 4B), strongly indicating that antisense oligonucleotide treatment activates p53 by increasing the levels of free p53 but not total p53.

Example 6

Induction of Apoptosis by Antisense Oligonucleotides

JAR cells (ATCC) were grown in DMEM medium supplemented with 1% FBS according to standard cell culture techniques. Cells were then treated for 30 hours with growth medium containing 400 nM of either antisense oligonucleotide AS5 (SEQ ID NO:28) complementary to a portion of MDM2-encoding RNA or control oligonucleotide M4 (SEQ ID NO:5), and 7 μg/ml lipofectin (Gibco BRL Paisley, UK). Treated cells were then photographed using a phase contrast microscope.

Figure 5A:
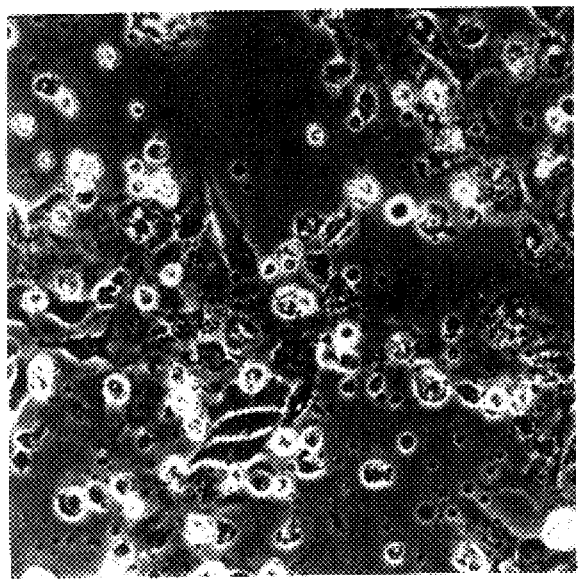
FIG. 5 is a reproduction of a photograph showing the morphology of cells treated with antisense oligonucleotides AS5 (panel A), and with control oligonucleotide M4 (panel B).
Figure 5B:
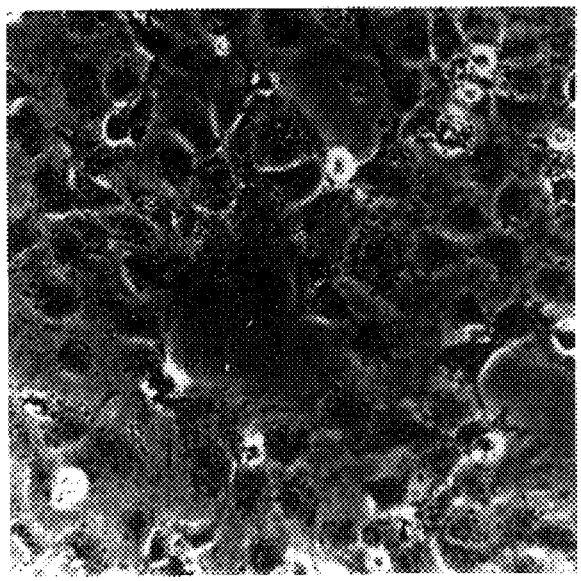

As shown in the FIG. 5, oligonucleotide AS5 induced significant cell death. Dying cells show the morphology characteristic of apoptosis, such as membrane blebbing and shrinkage. Control oligonucleotide M4 (SEQ ID NO:5) induced significantly less apoptosis.

Example 7

Interchromosomal DNA Cleavage in Floating Cells

JAR cells were treated for 24 hours as described in Example 6. Floating cells were harvested and chromosomal DNA was extracted according to standard techniques (Liu et al., Cell 86:147–157 (1996)). Purified DNA was then analyzed by agarose gel electrophoresis on a 2% agarose gel. Following electrophoresis the gel was stained with 0.5 μg/ml ethidium bromide.

Figure 6:
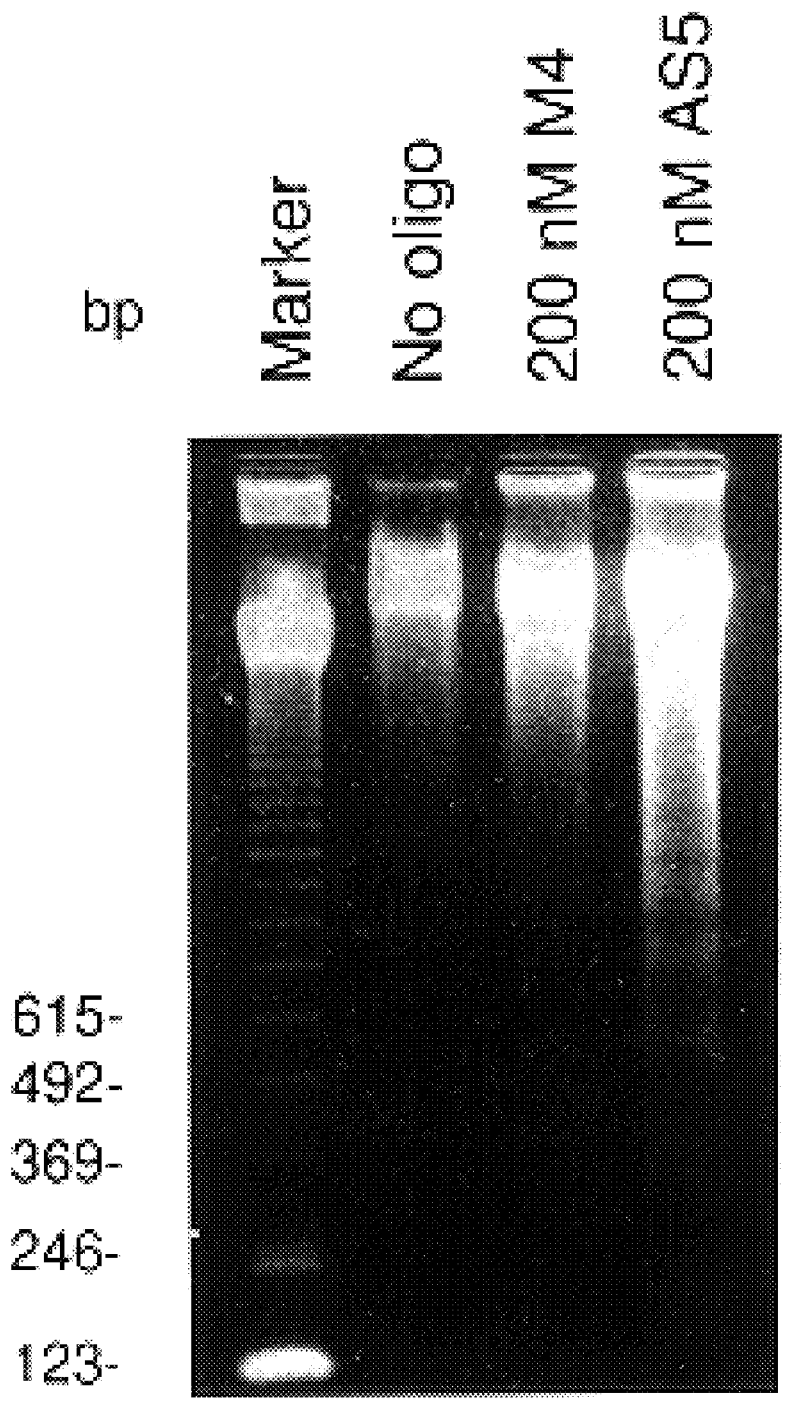
FIG. 6 is a reproduction of a photograph of an Ethidium Bromide stained agarose gel showing the size shift of chromosomal DNA of cells treated with the antisense oligonucleotides of the invention.

As shown in FIG. 6, genomic DNA purified from oligonucleotide AS5 treated cells showed nucleosomal-sized low molecular weight bands characteristic of apoptosis. Treatment of H1299 cells, (which lack p53) did not cause visible apoptosis (data not shown). These results suggest that oligonucleotide AS5 induced apoptosis is attributable to the activation of p53.

Example 8

Co-activation of p53 by AS5 and DNA-Damage

JAR cells stably transfected with BP100-luc as described in Example 4 were treated with the Topoisomerase I inhibitor camptothecin (CPT) and with 100 nM and 200 nM of either antisense oligonucleotide AS5 (SEQ ID NO:28), control oligonucleotide M4 (SEQ ID NO:5), or Lipofectin (no oligonucleotide control) for 48 hours. Induction of p53 activity was measured by luciferase assay as described in Example 4.

Figure 7A:
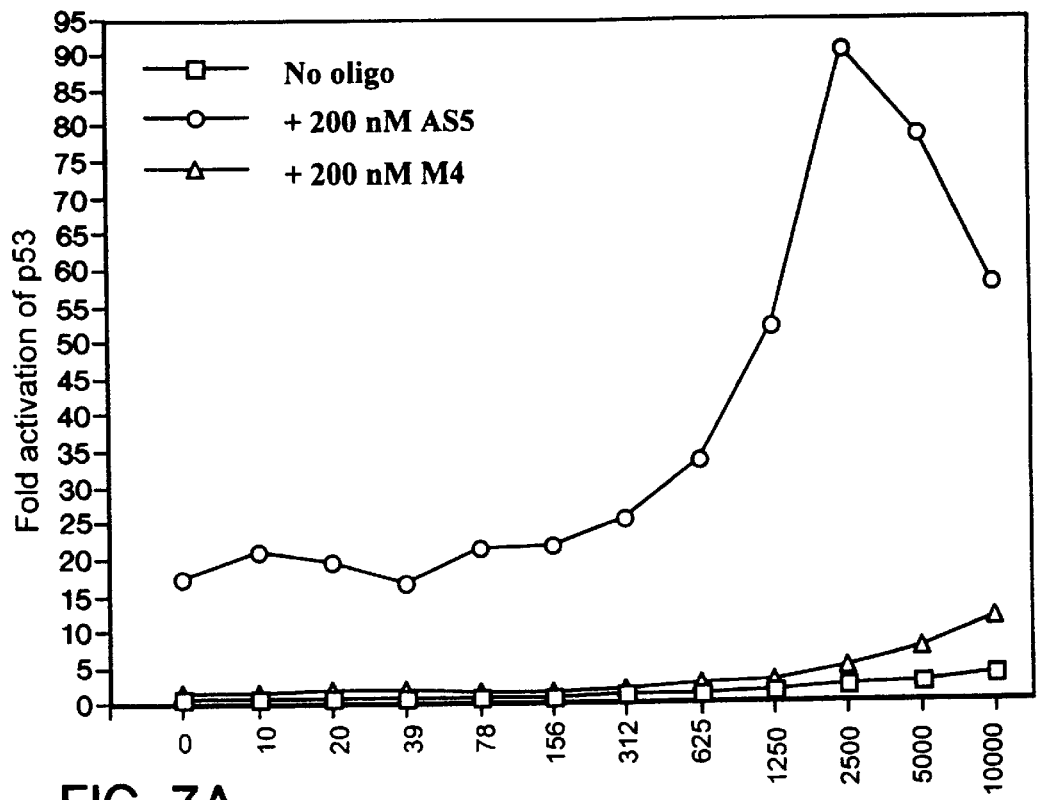
FIGS. 7A and B are graphical representations showing the relative luciferase activity in JAR cells transfected with BP100-luc that had been treated with camptothecin (CPT) and oligonucleotide AS5.
Figure 7B:
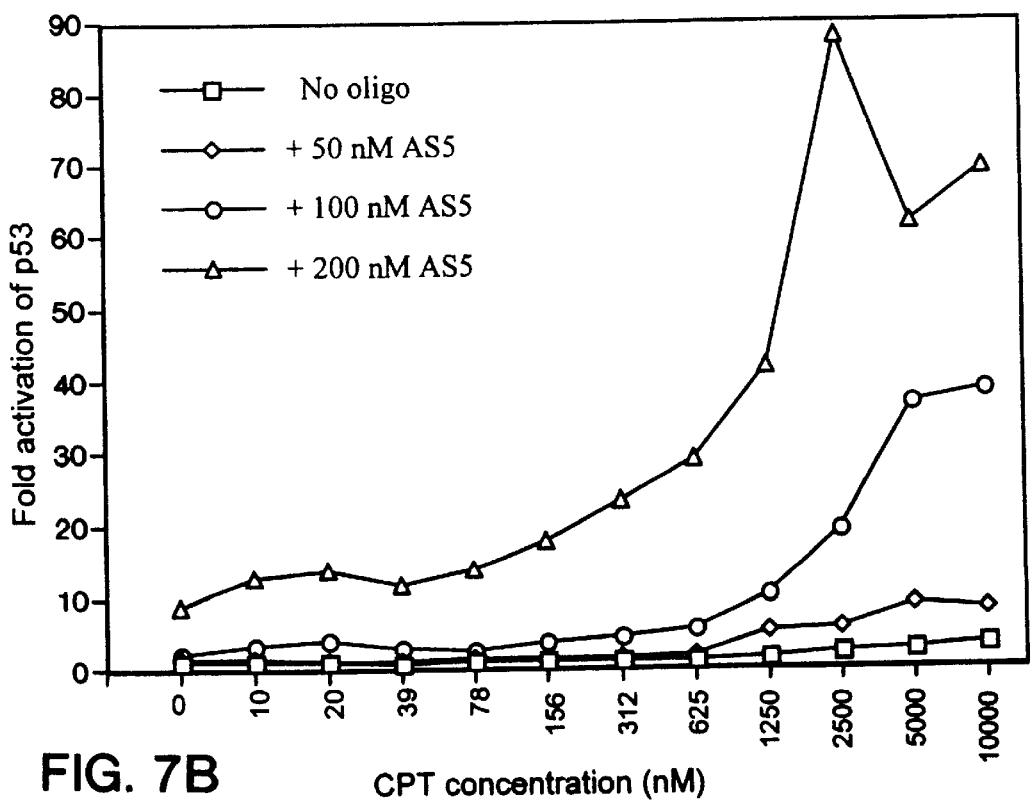
FIG. 7C is a graphical representation showing the relative luciferase activity in MCF-7 cells incubated with CPT, BP100-luc and CMV-lacZ reporter plasmids, and oligonucleotides in the presence of cationic lipids.
Figure 7C:
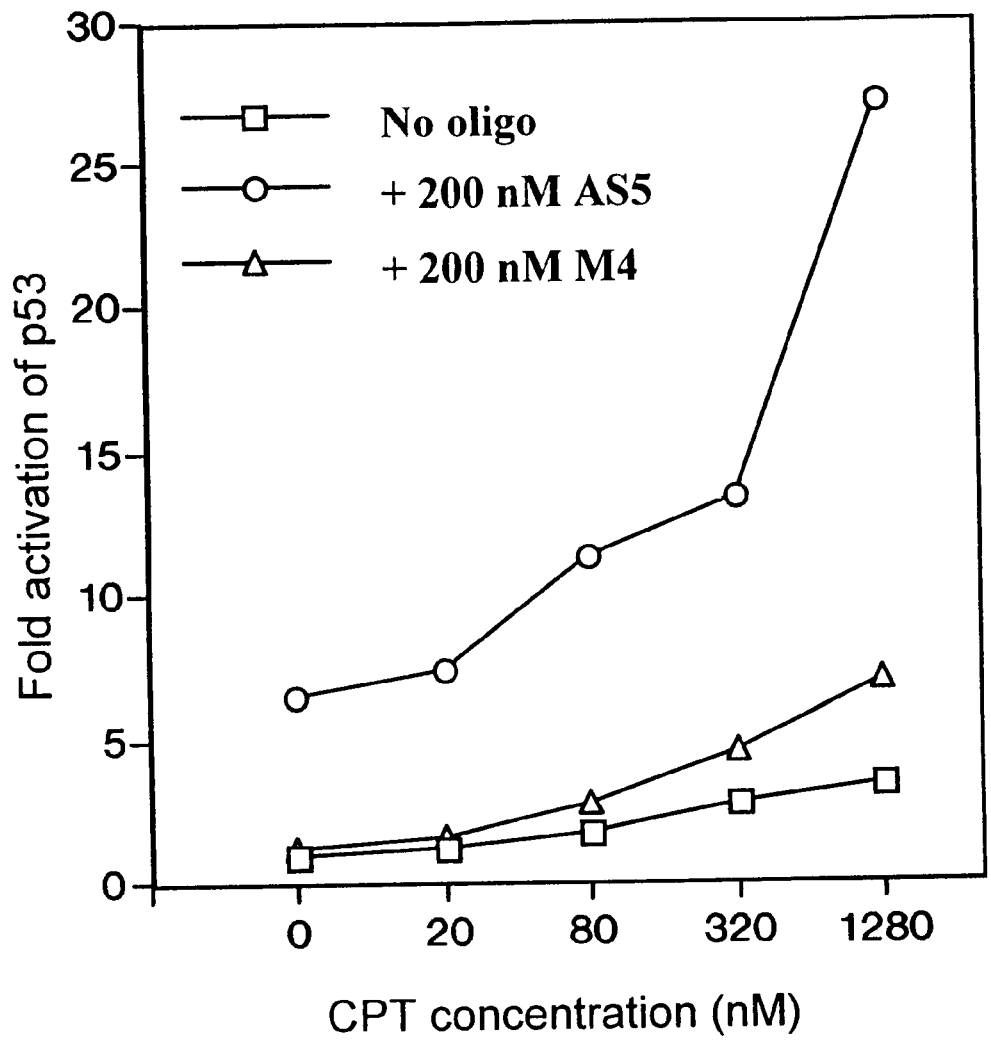

The results are displayed in FIGS. 7A–C. As shown in FIGS. 7A and B, CPT alone activated the p53 reporter only by 3–4 fold, incubation with 200 nM of oligonucleotide AS5 resulted in a 17-fold activation of the p53 reporter. Also as shown in FIGS. 7A and B, co-incubation with CPT and oligonucleotide AS5, however, resulted in up to 90 fold induction of p53 activity. A similar synergistic effect between AS5 and CPT was also observed in MCF-7 cells, a breast tumor cell line with wild-type p53 but no amplification of mdm2 (FIG. 7C). These results demonstrate that inhibition of mdm2 can synergistically cooperate with the effect of DNA damage and induce p53 transcriptional activity to high levels.

Examples 9–14

Investigation of Oligonucleotides Targeted to Regions Around the AS5 and AS7 Targeted Regions Antisense oligonucleotides targeted to AS5 (SEQ ID NO:28) and AS7 (SEQ ID NO:29) sequences within the mdm2 RNA were found to be the most effective in inducing p53 activity among the initial antisense oligonucleotides tested. This prompted us to further investigate antisense oligonucleotides targeted to the region around where the AS5 and AS7 oligonucleotides were targeted. Antisense oligonucleotides SEQ ID NOs: 35–46 were selected to target (i.e., be complementary to) sequences SEQ ID NOs: 13–24 within the human mdm2 mRNA, which target sequences overlapped or flanked the AS5 and AS7 target sequences. See Table 1, supra.

The following protocols were employed in each of the experiments disclosed in Examples 9–14, unless otherwise noted.

Figure 8A:
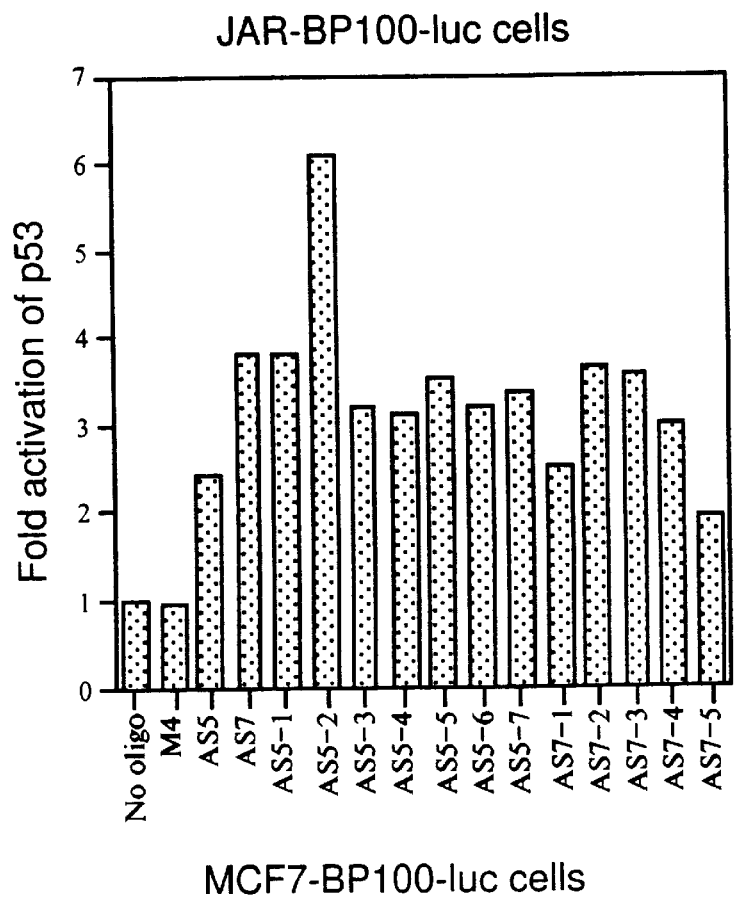
FIGS. 8A and 8B display the activation of p53 in JAR-BP100luc and MCF7-BP100luc cells by antisense oligonucleotides AS5-1 to AS5-7 and AS7-1 to AS7-5.
Figure 8B:
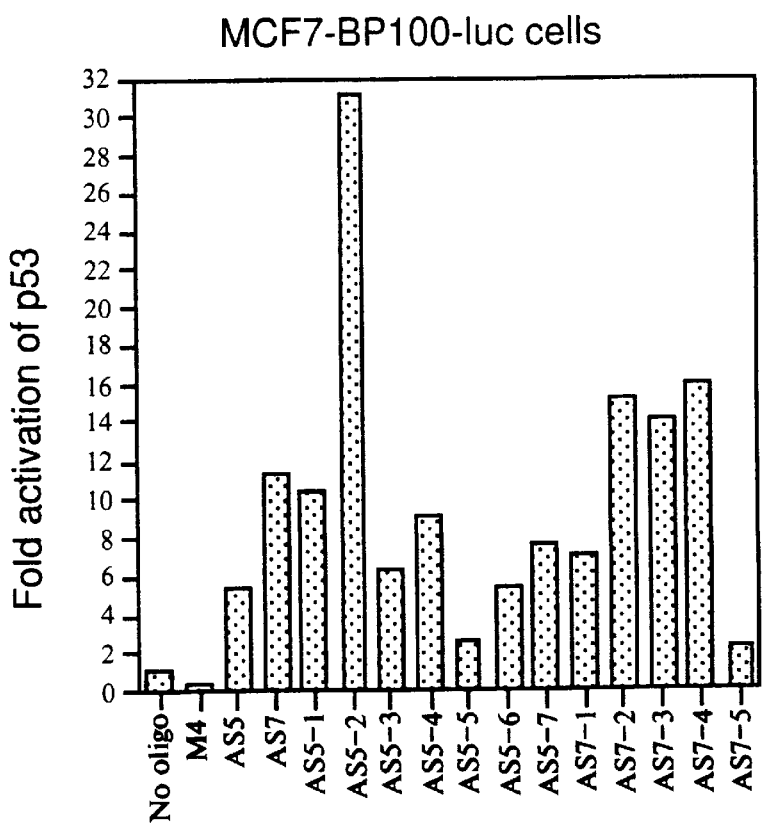

Synthesis of oligodeoxynucleotides. Phosphorothioate oligodeoxynucleotides were synthesized using, β-cyanoethyl phosphoramidite chemistry on an automated synthesizer (Expedite 8909, Perceptive Biosystems, Framingham, Mass.) and purified by preparative reverse-phase high performance liquid chromatography. Twelve 20-mer phosphorothioate antisense oligodeoxynucleotides (AS5-1 to AS5-7 and AS7-1 to AS7-5) were synthesized for this screen (FIG 8). A 2 bp mismatch control antisense oligonucleotide (AS2M2: 5'-TGACACTTGTT-CTTACTCAC-3'; SEQ ID NO: 25) and a 4 bp mismatch control antisense oligodeoxynucleotide (AS2M4: 5'-TGACTCTTGTCCTTACTCAC-3'; SEQ ID NO: 26) targeted to the S5-2 sequence of human mdm2 RNA were also synthesized. The oligodeoxynucleotide K (SEQ ID NO: 6) was a control against an unrelated target.

Cell lines. JAR, JEG-3, SJSA, MCF-7, U87-MG, SK-N-SH, U2OS, Caski, C33A, DLD-1, and A549 cells were obtained from the ATCC. WI-38, JeKin, HepG2, LS180, HT1080, G361, PA-1, and Lncap cells were obtained from the cell culture core lab of LSU Medical Center. H 1299, MCF-7, MDA-MB-231, and Hela cells were from Dr. Arnold J. Levine (Princeton University). The 101 cell line was provided by Dr. James Gnarra (LSU Medical Center). The SLK cell line was kindly provided by Dr. Om Prakash (Ochsner Foundation). All cells were grown in DMEM with 10% fetal bovine serum (FBS).

Antisense oligonucleotide treatment. Cells were cultured in DMEM medium with 10% FBS. Cell lines normally grown in other types of medium were also adapted to growth in DMEM with 10% FBS before the treatment. Before addition of oligonucleotides, cells were refed with DMEM containing 1% FBS. Lipofectin (Gibco BRL) was incubated with serum-free DMEM medium for 45 min, then mixed with the oligonucleotides for 10 min and added to the cell culture. The final concentration of Lipofectin was 7 µg/ml, final concentration of FBS was 0.75%. Cells were incubated with oligonucleotides and Lipofectin for 18–24 hr as indicated.

Western blot. Cells were lysed in RIPA buffer (50 mM Tris, pH 7.4, 150 mM NaCl, 1% Triton X-100, 0.1% SDS, 1% Na deoxycholate) and 100 µg of the protein lysate were fractionated by SDS-polyacrylamide gel electrophoresis (SDS PAGE) and transferred to Immobilon P filters (Millipore). The filters were blocked for 5 min with 5% non-fat dry milk, incubated with anti-p53 antibody DO-1 or an anti-human MDM2 rabbit serum, then incubated with protein A-peroxidase (Promega), washed, and developed using the ECL-plus reagent (Amersham). All incubations wore carried out in phosphate-buffered saline with 5% non-fat milk and 0.1% Tween-20.

Stable transfection of cell lines. Cells were co-transfected with the BP100-luciferase reporter plasmid or pActin-E6 plasmid and a G418-resistant marker plasmid pCMV-neo-Bam using the calcium phosphate precipitation method. Transfected cells were grown in medium with 750 µg/ml G418 until colonies appeared. Individual colonies were isolated and expanded into cell lines. The JAR-BP100-luc is a clonal cell line isolated by diluting a pool of BP100-luciferase transfected JAR cells from a previous experiment. Chen et al., *Proc. Natl. Acad. Sci. U.S.A.* 95, 195–200 (1998).

Immunofluoresence staining. For p53 staining, cells were treated with oligonucleotides for 20 hr, fixed with acetone-methanol (1:1) for 3 min, then blocked with PBS+10% normal goat serum (NGS) for 20 min, and incubated with Pab1801 hybridoma supernatant for 2 hr. In order to stain for MDM2, cells were fixed in 4% paraformaldehyde in PBS for 20 min, blocked with PBS+10% NGS for 20 min, and incubated with 2A9 hybridoma supernatant at 1/100 dilution in PBS+10% NGS for 2 hr. Slides were washed with PBS+0.1% Triton X-100, incubated with FITC-goat-anti-mouse IgG in PBS+10% NGS for 1 hr, washed with PBS+ 0.1% TritonX-100 and mounted.

Determination of p53 half life. SJSA cells were treated with 200 nM AS2 for 20 hr. Cells were incubated with DMEM (without methionine) with 2% dialyzed FBS, 50 uCi/ml 35S-EXPRESS (NEN) for 2 hr and refed with regular medium. Sample plates were collected at indicated time points and lysed with lysis buffer (50 mM Tris, pH 8.0, 5 mM EDTA, 150 mM NaCl, 0.5% NP40, 1 mM PMSF). Cell lysates with identical levels of radioactivity ($\sim 2 \times 10^7$ CPM) were immunoprecipitated with Pab421 and Pab1801, washed with 50% SNNTE buffer (25 mM Tris, pH 7.4, 2.5 mM EDTA, 2.5% sucrose, 1% NP-40, 250 mM NaCl), and fractionated by SDS PAGE. P53 was detected by autoradiography.

Determination of cell proliferation rate. Cells were treated with 100 nM of oligonucleotides for 20 hr, labeled with BrdU for 2 hr, and incubated with MTS reagent (Promega) for 1 hr. Relative cell viability was determined by measuring OD at 490 nm (reduction of MTS substrate by mitochondria activity). Cells were then fixed and the level of BrdU incorporation was determined using a chemiluminscence ELISA assay (Boehringer Mannheim). The rate of DNA synthesis was determined as BrdU incorporation/OD 490.

Example 9

Optimization of MDM2 Antisense Oligonucleotide

JAR cells or MCF7 cells were stably transfected with the p53-responsive BP100-luciferase reporter gene were incubated with 100 nM of oligonucleotides AS5-1 to AS5-7 and AS7-1 to AS7-5 in the presence of cationic lipids for 20 h. p53 transcriptional activation function was determined by measuring luciferase activity. Oligonucleotides AS5 and AS7 were used as positive controls. A missense mutant of AS5M4 was used as a negative control.

The results shown in FIG. 8 demonstrate that all of the oligonucleotides tested were effective in induction of p53 activity in both tumor cell lines. The oligonucleotide AS5-2 is the most potent in activation of p53 and was further tested in animal tumor models, infra.

Figure 9B:
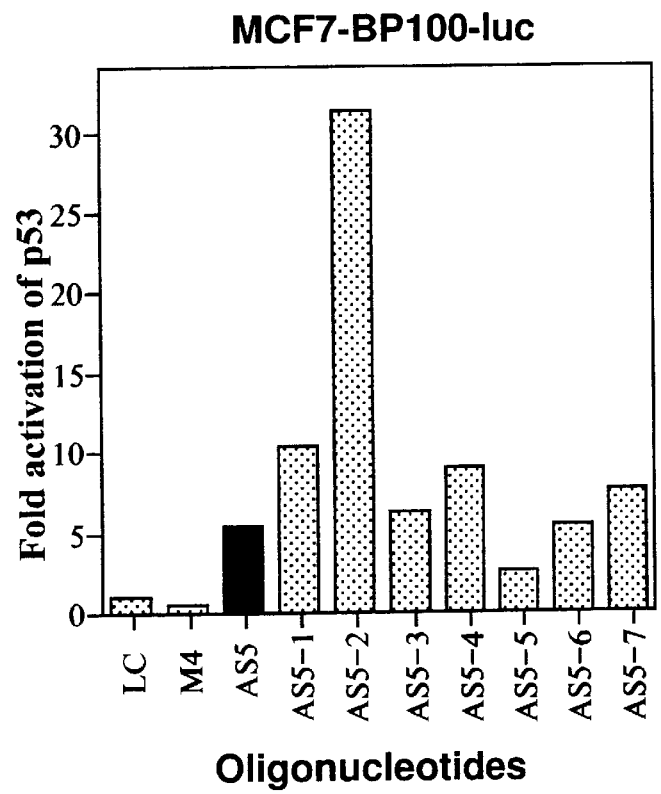
FIG. 9B displays the results of the screening of mdm2 antisense oligonucleotides. MCF-7 cells stably transfected with the BP100-luc reporter were treated with 50 nM of MDM2 oligonucleotides for 20 hr. p53 transcriptional activity was determined as luciferase activity/unit protein. M4 is a 4 bp mismatch control of AS5.
Figure 9C:
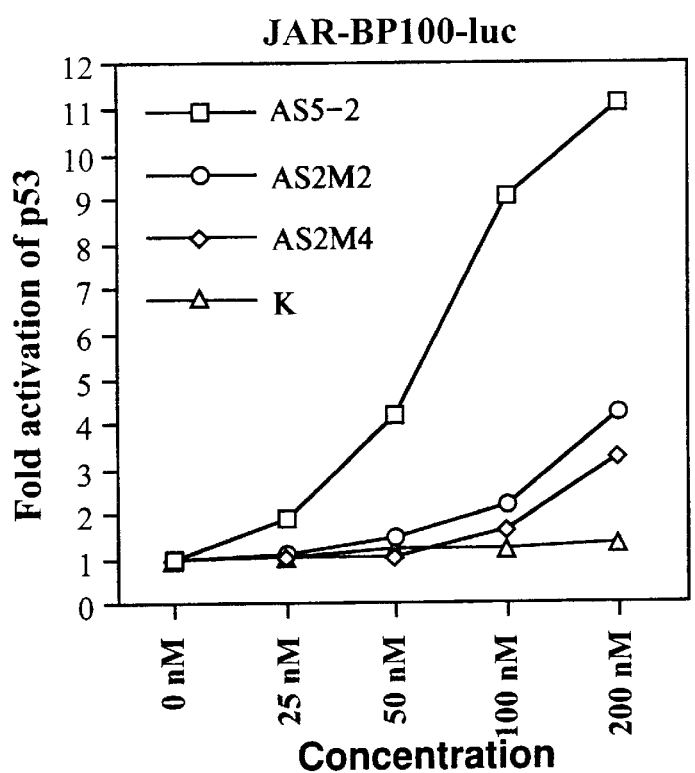
FIG. 9C displays the results of activation of p53 by HDMAS5-2, showing that it is sequence specific. JAR cells stably transfected with the BP100-luc reporter were treated with HDMAS5-2, mismatch control oligonucleotides of HDMAS5-2 (AS2M2: 2 bp mismatch. AS2M4: 4 bp mismatch) and an unrelated oligonucleotide K.

The p53 activation assays demonstrated that several of the secondary oligonucleotides were more effective than AS5 in causing activation of p53 (FIG. 9B). The AS5-2 oligonucleotide was the most potent of this group and was chosen for further characterization. AS5-2 was five-fold more efficient than AS5 in MCF-7cells (FIG. 9B) and two-fold more efficient than AS5 in JAR cells (not shown) at a concentration of 50 nM. Similar to the AS5 oligonucleotide, AS5-2 treatment also inhibited MDM2 protein expression (not shown). The effect of AS5-2 is sequence specific. Introduction of two or four nucleotide mismatches into the sequence significantly inhibited its ability to activate p53 (FIG. 9C). When AS5-2 and AS5 (each 20 nucleotides) were shortened to 18 nucleotides from one or both ends, the ability to activate p53 was also significantly reduced (not shown).

Example 10

Apoptotic Function of AS5-2 is p53-dependent

Similar to the parent AS5 oligonucleotide, AS5-2 also induces apoptosis in JAR cells. In order to further delineate whether AS5-2 induces apoptosis through activation of p53, a JAR cell line expressing the E6 oncogene of HPV16 was created (JAR-E6). Expression of E6 under the actin promoter resulted in degradation of p53, as demonstrated by the loss of p53 protein in a Western blot (FIG. 10). Interestingly, the level of mdm2 expression also decreases significantly in JAR-E6 cells, suggesting that in addition to gene amplification, activation by p53 is an important mechanism of mdm2 overexpression in this cell line.

When treated with 200 nM of AS5-2, which efficiently induced apoptosis in parental JAR cells, JAR-E6 cells showed little apoptosis (FIG. 10). This result suggests that AS5-2 induces apoptosis through specific activation of p53.

Example 11

Induction of P53 Accumulation by Inhibition of MDM2 in Different Cell Lines

The strong activation of p53 in MCF-7 cells by AS5-2 (FIG. 9) prompted us to further examine its effect on p53. MCF-7 cells predominantly contain a cytoplasmic form of p53 (Takahashi et al., Mol Carcinog 8:58–66 (1993)) and display predominantly cytoplasmic fluorescence when stained using anti-p53 monoclonal antibody Pab1801. After treatment with 200 nM AS5-2 for 20 hr, many MCF-7 cells showed intense nuclear p53 staining (FIG. 11). The parent AS5 oligonucleotide also showed a similar, but weaker, ability to induce p53 accumulation (not shown), and the control oligonucleotide K did not induce p53 (FIG. 11). This suggests that nuclear p53 in this cell line is being actively degraded by MDM2, not simply being sequestered into the cytoplasm.

In order to determine whether MDM2 also exhibits a similar role in other tumors containing cytoplasmic p53, the neuroblastoma cell line SK-N-SH was tested. Neuroblastomas rarely have p53 mutations but often contain p53 in the cytoplasm. SK-N-SH cells express cytoplasmic wild-type p53 and exhibit a reduced ability to undergo cell cycle arrest after DNA damage. Moll et al., Proc. Natl. Acad. Sci. U.S.A. 92:4407–4411 (1995); Goldman et al., Am. J. Pathol. 148:1381–1385 (1996). When treated with AS5-2, this cell line also displayed a strong accumulation of nuclear p53 in nearly 100% of the cells (FIG. 11). This result suggests that in addition to cytoplasmic sequestration, MDM2-mediated degradation is important for the loss of nuclear p53 in some tumors.

This test was then extended to a wide variety of tumor cell lines with wild-type p53. A total of 24 human tumor cell lines representing 15 different tumor types were treated with AS5-2 and stained for p53 expression. Cells were treated with 200 nM of AS5-2 or K oligonucleotide for 20 hr and p53 level was determined semi-quantitatively by immunofluorescene staining with Pab1801. Mdm2 levels in untreated cells were determined by staining with 2A9. The results, as shown in FIG. 11 and summarized in Table 2, infra, revealed that the low levels of wild-type p53 can be significantly stimulated by AS5-2, resulting in intense nuclear p53 staining. Two non-transformed human cell lines, WI-38 (lung fibroblast) and JeKin (skin fibroblast) also showed strong p53 accumulation after inhibition of MDM2 expression. Therefore, this p53 response due to loss of MDM2 is not unique to tumor cells.

TABLE 2

| Cell line | Origin | MDM2 level | p53 | Nuclear p53 level Basal | AS5-2 treated |
|---|---|---|---|---|---|
| JEG-3 | Choriocarcinoma | ++++ | Wt | ++++ | ++++ |
| JAR | Choriocarcinoma | ++++ | Wt | ++++ | ++++ |
| SJSA | Osteocarcoma | ++++ | Wt | − | ++++ |
| LS180 | Colon carcinoma | − | Wt | − | ++++ |
| HT1080 | Fibrosarcoma | + | Wt | + | ++++ |
| A172 | Glioblastoma | − | Wt | − | ++++ |
| U87-MG | Glioblastoma | − | Wt | + | ++++ |
| HepG2 | Hepatocarcinoma | + | Wt | + | ++++ |
| SLK | Kaposi sarcoma | − | ND | + | ++++ |
| 101 | Kidney tumor | − | Wt | + | ++++ |
| A549 | Lung tumor | + | Wt | + | ++++ |
| G361 | Melanoma | ++ | Wt | + | ++++ |
| SK-N-SH | Neuroblastoma | − | Wt | − | ++++ |
| MCF-7 | Breast carcinoma | + | Wt | + | ++++ |
| U20S | Osteosarcoma | + | Wt | ++ | ++++ |
| PA-1 | Ovarian teratoma | + | Wt/mt | − | ++++ |
| Lncap | Prostate carcinoma | − | Wt | + | ++++ |
| WI-38 | Lung Fibroblast | + | Wt | − | ++++ |
| JeKin | Skin fibroblast | − | Wt | + | ++++ |
| MDA-MB-231 | Breast carcinoma | ++ | Mt | ++++ | ++++ |
| DLD-1 | Colon carcinoma | ++ | Mt | ++++ | ++++ |
| C33A (HPV-) | Cervical carcinoma | +++ | Mt | ++++ | ++++ |
| Hela (HPV+) | Cervical carcinoma | − | Wt | − | − |
| Caski (HPV+) | Cervical carcinoma | − | Wt | − | − |
| H1299 | Lung tumor | − | Null | − | − |
| SK-N-MC | Neuroblastoma | − | Null | − | − |

−: not detectable;
+: weak staining in most cells or a subset of cells;
++++: strong staining in most or all cells.
ND: not determined.

These results also reproduce our previous observation that in certain tumor cells (JAR, JEG-3) with high levels of stable p53, inhibition of MDM2 expression did not result in a significant increase of p53 level. The coexistence of high levels of p53 and MDM2 suggests that the ability of MDM2 to promote degradation of p53 is lost in these cells.

Treatment of tumor cells with homozygous mutant p53 also did not lead to further accumulation of p53, which was already at a high level. A tumor cell line with both wild-type and mutant p53 alleles (PA-1 ) also contained inducible p53 and underwent apoptosis after AS5-2 treatment (see below). Finally, treatment of HPV-positive cervical cancer cell lines did not induce p53 accumulation, suggesting that HPV E6-mediated degradation of p53 is independent of MDM2 function.

Example 12

Inhibition of MDM2 Expression Prolonged P53 Half Life

Figure 12A:
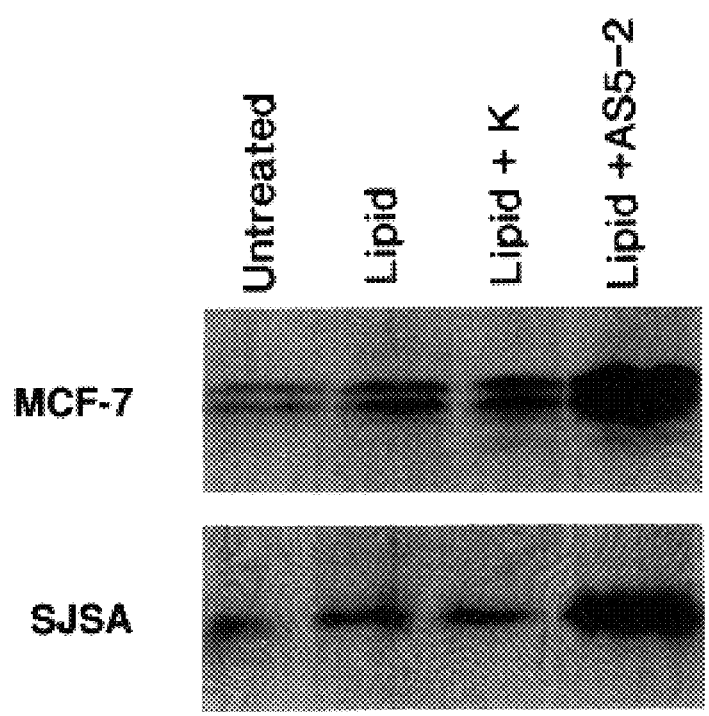
FIG. 12A and B display autoradiograms demonstrating stabilization of p53 by inhibition of mdm2 expression.

The increase of p53 after inhibition of mdm2 expression can result from an increased rate of p53 synthesis or protein stabilization. To directly test these possibilities, the p53 half-life in AS5-2 treated SJSA cells was determined by a pulse-chase radioactive labeling experiment. SJSA cells have mdm2 gene amplification and exhibit a highly inducible wild-type p53 after AS5-2 treatment (FIG. 11, FIG. 12A). This cell line does not undergo significant apoptosis after AS5-2 treatment, thus can provide sufficient material for analysis.

Figure 12B:
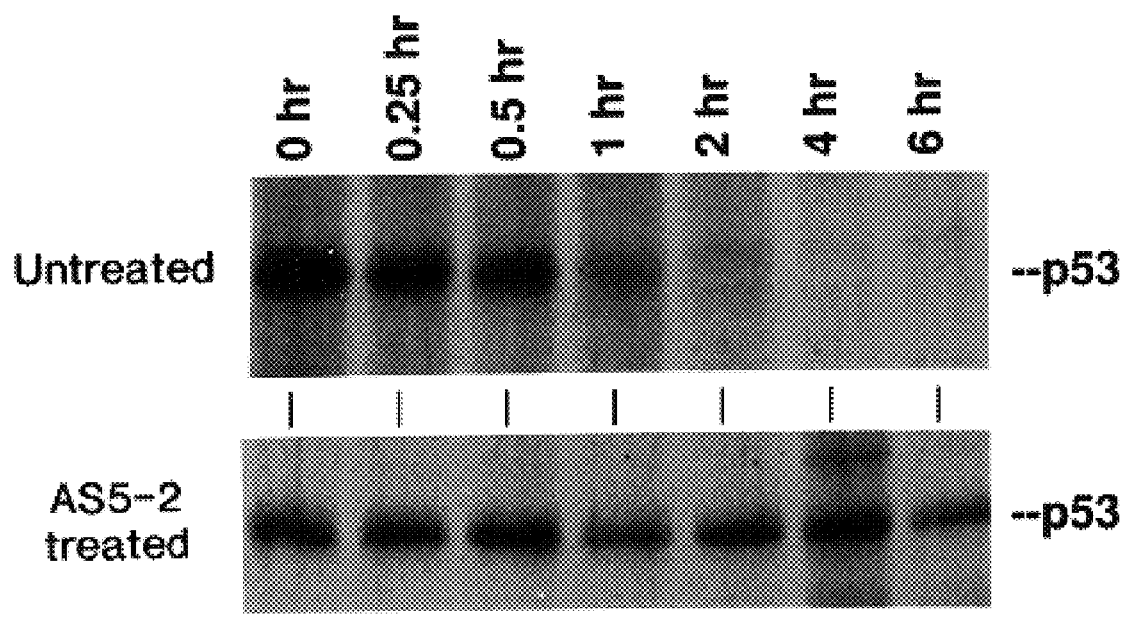
FIG. 12B shows the results of the determination of p53 half life. SJSA cells were treated with 200 nM AS5-2 for 20 hr and the rate of p53 degradation was determined by a pulse-chase experiment. The half life of p53 was ~0.5 hr in untreated SJSA cells and >4 hr in AS5-2 treated cells as determined by desitometric analysis.

SJSA cells were treated with 200 nM AS5-2 for 20 hr and pulse labeled with $^{35}S$-methionine for 2 hr. The level of p53 was determined at various times after addition of excess cold methionine to prevent further synthesis of radioactive p53. The result showed that the half life of p53 is increased from ~0.5 hr in untreated SJSA cells to >4 hr in AS5-2 treated cells. Furthermore, the amount of radioactive MDM2 synthesized during the 2 hr pulse labeling period did not differ significantly in treated and untreated cells (FIG. 12B). Therefore, the rise in p53 level after inhibition of MDM2 expression appears to be due to the stabilization of p53 and not to its increased synthesis.

Example 13

Inhibition of MDM2 Expression Induces Functional p53

Figure 13A:
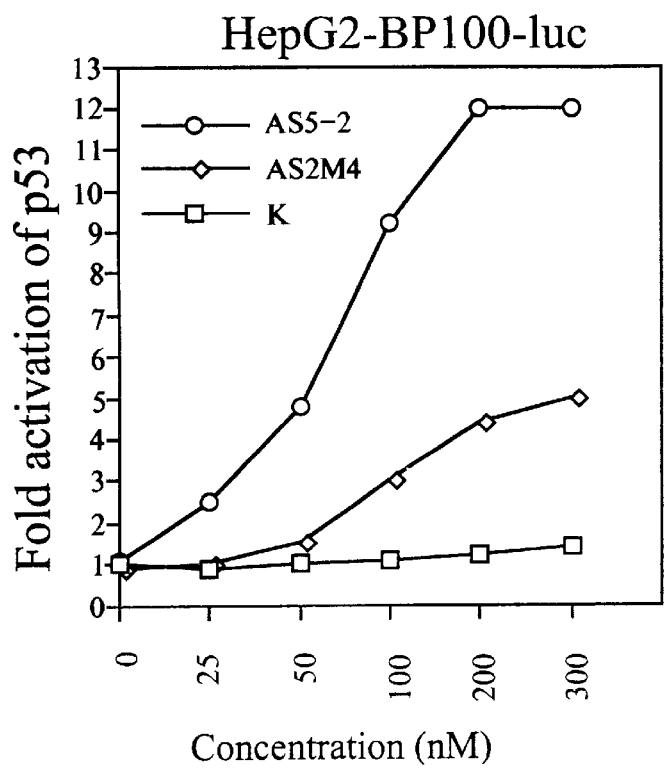
FIG. 13A and 13B shows the results of induction of p53 transcriptional activation function. Cells stably transfected with the BP100-luciferase reporter were treated with antisense oligonucleotides at indicated concentrations for 20 hr. Luciferase activity/unit protein was determined and the magnitude of induction was shown compared to cells not treated with oligonucleotides. AS2M4: a 4 bp mismatch control of AS5-2. K: an unrelated oligonucleotide.
Figure 13B:
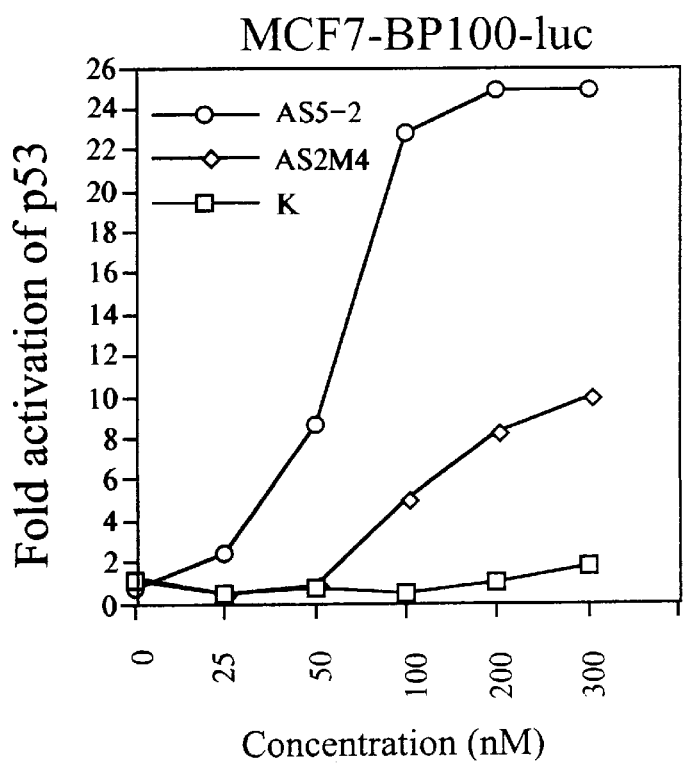
Figure 15A:
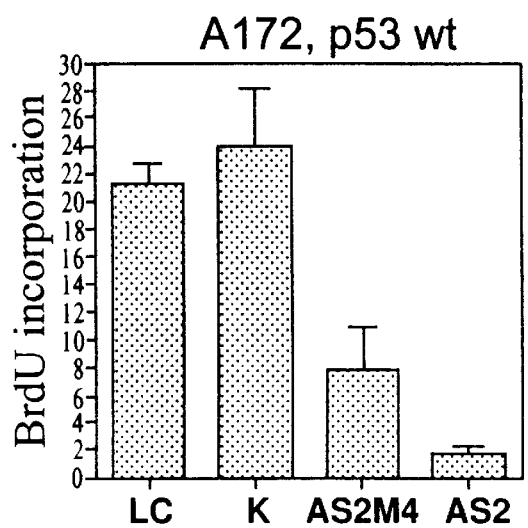
FIGS. 15A–D shows the inhibition of DNA synthesis by mdm2 antisense oligonucleotides. Cells were treated with 100 nM of oligonucleotides for 20 hr and labeled for 2 hr with BrdU. Incorporation rate of BrdU was determined by an ELISA assay and normalized to the number of viable cells. H1299 and 10(1) cells are human and mouse cells devoid of p53. LC: lipofectin treatment alone.
Figure 15B:
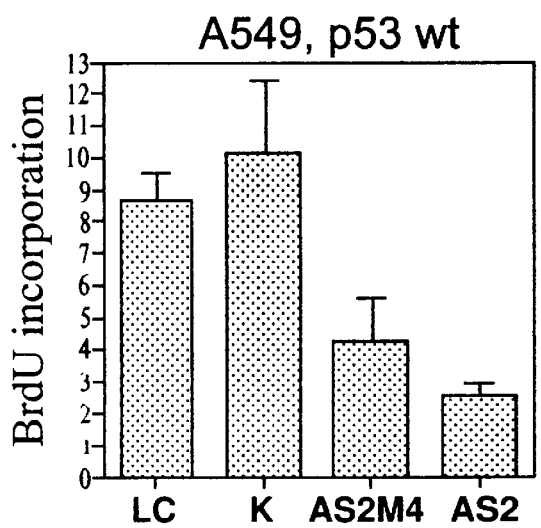
Figure 15C:
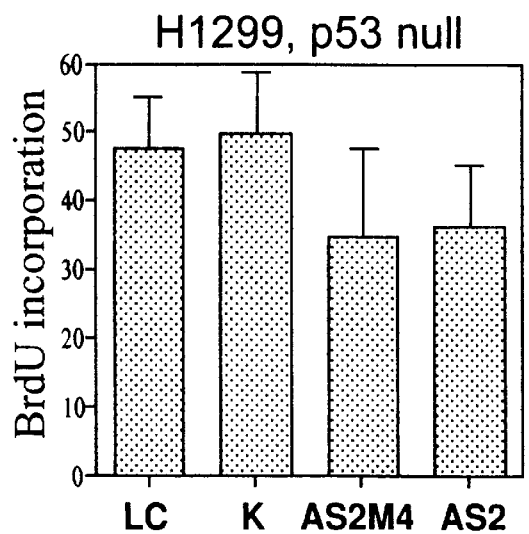
Figure 15D:
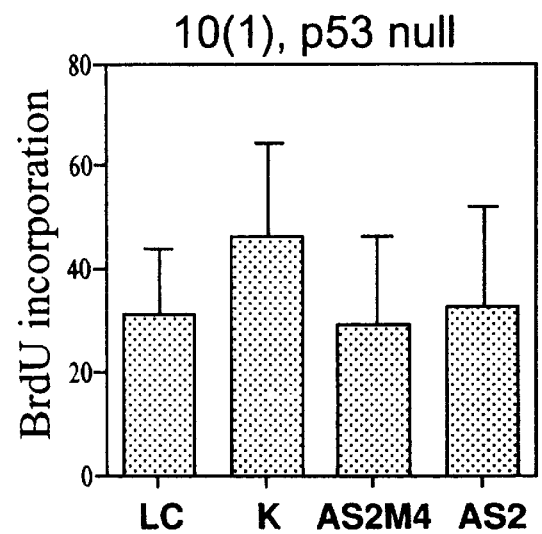

In order to determine whether the p53 protein that accumulates after inhibition of mdm2 is functionally active, a p53-responsive BP100-luciferase reporter plasmid was transfected into several representative cell lines. Stably transfected cells were then treated with AS5-2 or control oligonucleotides. The results showed that a strong induction of p53 transcription function occurs after inhibition of mdm2, demonstrating that the p53 accumulated after inhibition of mdm2 is highly active (FIG. 13). The magnitude of p53 transcription activation is consistent with the fact that most of the p53 accumulation occurs in the nucleus, which has a low basal level of p53. The 4 bp mismatch control oligonucleotide has significantly reduced efficiency in activation of p53, particularly at low concentrations.

Example 14

Inhibition of MDM2 Leads to Growth Arrest and Apoptosis

A number of cells lines were treated with 200 nM AS5-2 for 20 hr. A significant amount of cell death was evident in many of the tumor cell lines tested (FIG. 14). In several cases, cells rounded up, displayed membrane ruffling and blebbing characteristic of apoptosis, and detached from the culture surface. Thus, it appears that the level of p53 activation achieved by treatment with AS5-2 is sufficient to induce cell death through apoptosis in some of the cell lines examined.

Some of the tumor cell lines as well as two non-transformed cell lines (WI-38 and Jekin) showed little cell death after a 20 hr AS5-2 treatment. Since p53 activation can lead to apoptosis or cell cycle arrest, dependent on the level of p53 and the status of the cell, several of these cell lines were further tested for growth arrest by AS5-2. Cells were treated with AS5-2 or control oligonucleotides for 20 hr, and DNA synthesis was quantitated by BrdU incorporation. The number of viable cells was determined by incubation with the MTS reagent. The results show that in cell lines that do not undergo significant apoptosis after AS5-2 treatment, the rate of DNA synthesis is reduced (FIG. 15). This effect is weaker with a 4 bp mismatch control oligonucleotide and is not observed with the unrelated oligonucleotide K. In contrast, the p53-null cell lines H1299 (human) and 10(1) (mouse) (Harvey and Levine, *Genes. Dev.* 5, 2375–2385 (1991)) did not undergo significant growth inhibition. Therefore induction of p53 by inhibition of mdm2 can lead to growth arrest or apoptosis.

Example 15

In Vivo Studies of Anti-MDM2 Antisense Oligonucleotides

A new generation of mixed-backbone oligonucleotide was designed with the same sequence as AS5-2 and used in in vivo studies. The structures of these oligos are illustrated below in Table 3; all internucleotide linkages are phosphorothioates and the underlined nucleotides are 2'-O-methyl substituted.

TABLE 3

| Name | SEQ ID NO: | Sequence |
|---|---|---|
| AS5-2 | 28 | 5'-TGA CAC CTG TTC TCA CTC AC-3' |
| AS5-2H | 47 | 5'-<u>UGA</u> CAC CTG TTC TCA C<u>UC</u> <u>AC</u>-3' |
| AS5-2HM | 48 | 5'-<u>UGA</u> GAC CAG TTG TCA G<u>UC</u> <u>AC</u>-3' |

Compared with PS-oligos, hybrid oligos have increased in vivo stability, decreased degradation rate, less host toxicity, and, more importantly, increased therapeutic effects (Zhang et al., Biochem. Pharm. 49:929–939 (1995); Zhang et al., Biochem. Pharm. 50:545–556 (1995); Agrawal and Zhang in Antisense research and Applications, pp. 525–543 (S. Crooke, ed., Springer-Verlag, Heidelberg 1997); and Zhao et al., Biochem. Pharm,. 51:173–182 (1996)). Therefore, we anticipated that AS5-2H would have a better therapeutic effect in vivo than its PS-oligonucleotide counterpart. The tumor cell lines, SJSA and JAR, were cultured under the same conditions as in in vitro studies (Chen et al., *PNAS* 1998, supra). Human cancer xenograft models were established using the methods reported previously (Cai et al., Intl. J. Oncol. 10:953–960 (1997); and Zhang et al, Intl. J. Oncol. 101147–1156 (1997)). Female nude mice (five week old) were used in the study. Cultured SJSA and JAR cells were harvested from the monolayer cultures, washed twice with DMEMF-12 HAM medium, resuspended in DMEM, and injected s.c. (20×106 cells, total volume 0.2 ml) into the left inguinal area of the mice. The animals were monitored by general clinical observation, body weight, and tumor growth. The animals with SJSA xenografts were used in the chemotherapy study when the tumor size reached 150 mg. Animals with JAR cells were treated when the tumor size reached 2,000 mg. The animals bearing human cancer carcinoma xenografts were randomly divided into treatment groups and a control group (6–10 mice/group). Oligonucleotides dissolved in physiological saline (0.9% NaCl) were administered by ip injection at various daily doses, 5 consecutive days per week. The control group received physiological saline only.

To determine the potential synergistic effects between mdm2 inhibition and DNA damage, oligonucleotides and HCPT were co-administered to tumor bearing mice. Tumor growth was monitored using the methods previously reported (74,75). Tumor weight (g) was calculated by the formula, $½·a·b^2$, where "a" is the long diameter (cm) and "b" is the short diameter (cm) of the tumor. At the end of the experiment, tumors were removed, weighed, and then fixed for pathology evaluation.

Figure 16:
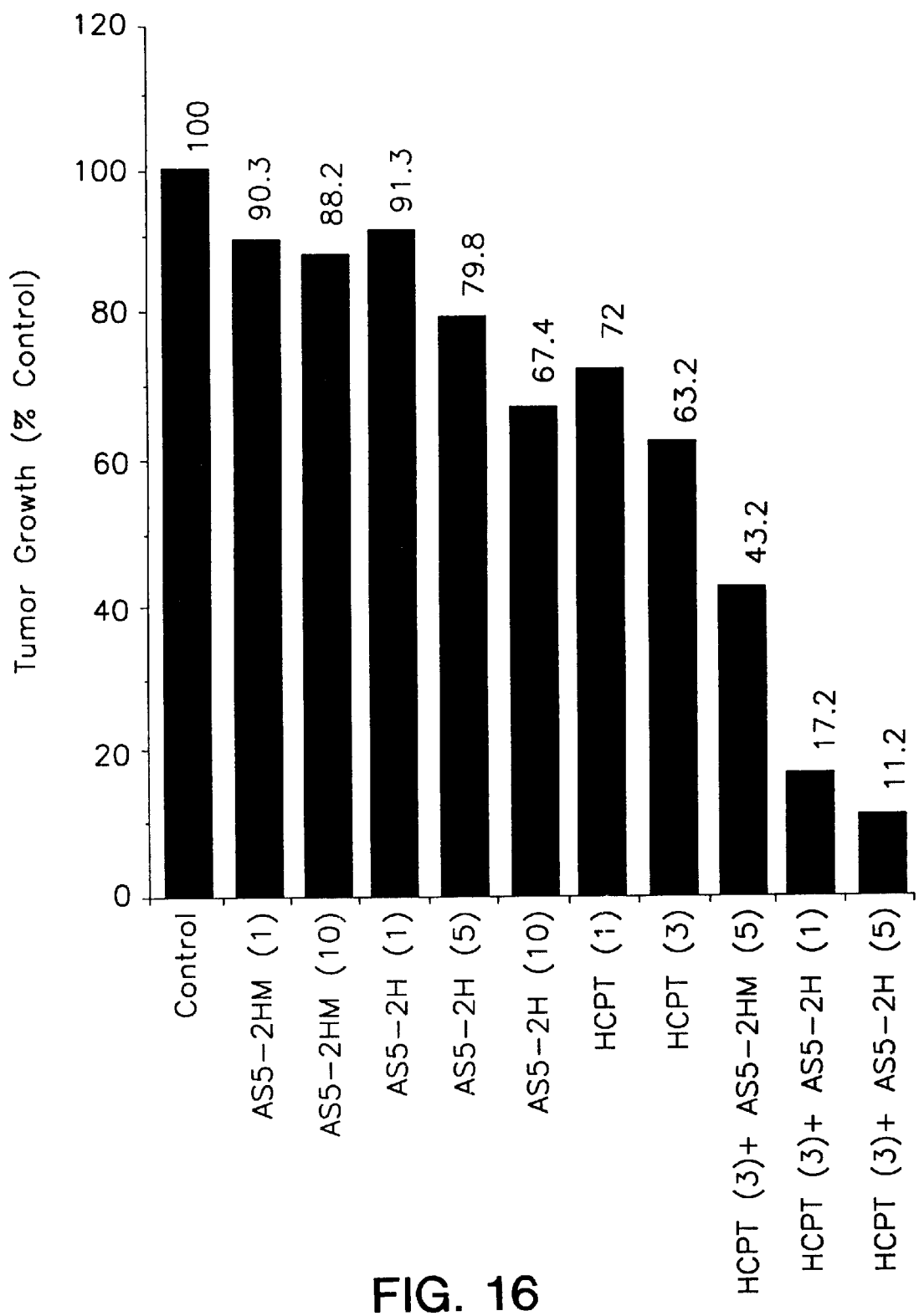
FIG. 16 displays anti-tumor activities of anti-msm2 oligos administered alone or in combination with topoisomerase I inhibitor10-hydroxycamptothecin (HCPT). Animals bearing SJSA xenografts(average 150 mg) were treated with drugs by ip injection, at designated daily doses, 5 dose/week. Control: saline; AS5-2HM (mismatch control oligonucleotide); AS5-2H: anti-MDM2 hybrid oligonucleotide designed according the sequence of AS5-2; HCPT: a topoisomerase I inhibitor that induces DNA breaks. The numbers in parenthesis are daily doses (mg/kg/day).
Figure 17:
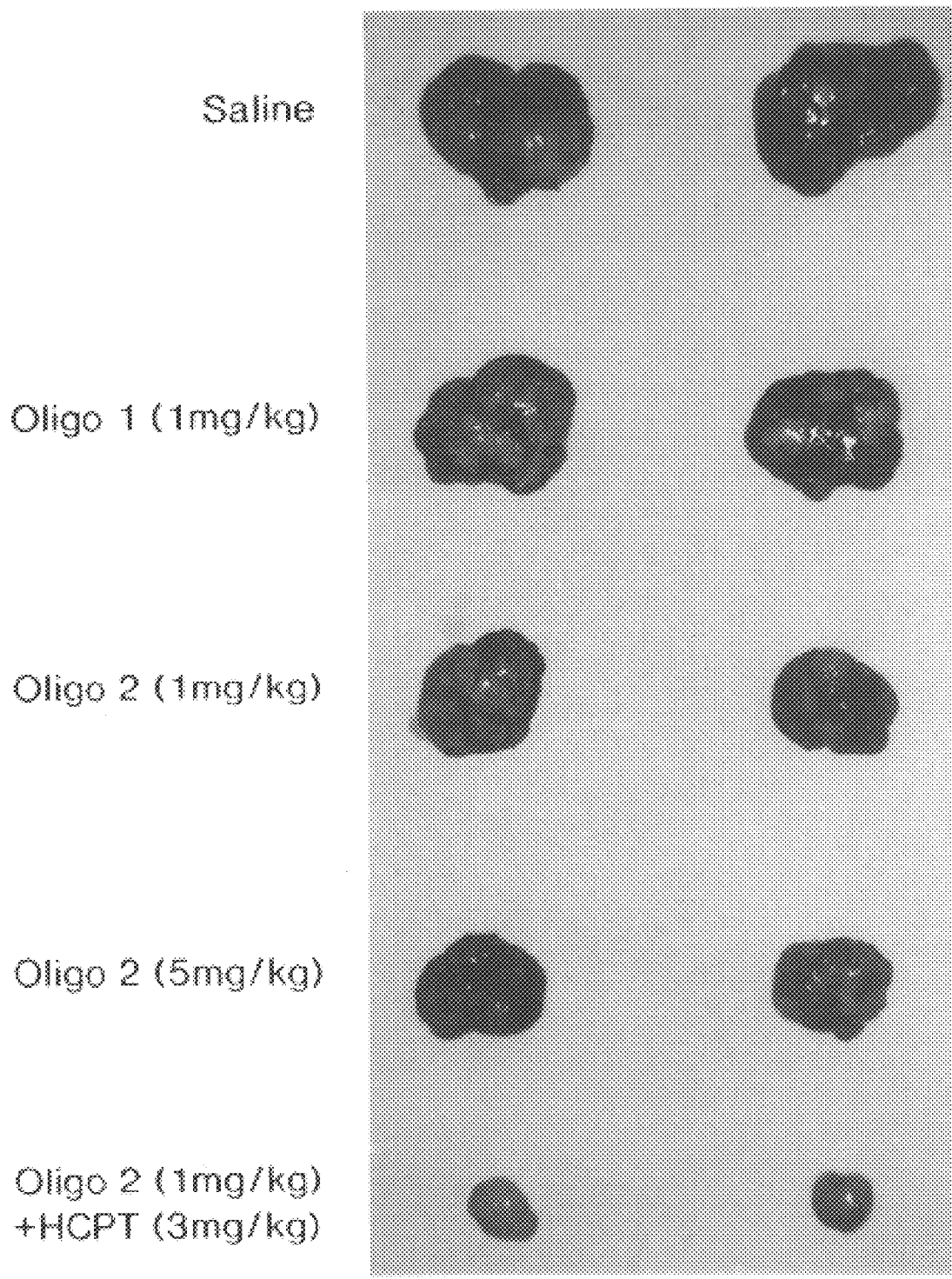
FIG. 17 displays representative tumor sizes of mice treated with antisense oligonucleotides according to the invention (alone or in combination with topoisomerase I inhibitor 10-hydroxycamptothecin (HCPT). Animals bearing SJSA xenografts (average 150 mg) were treated with drugs by ip injection at the designated daily dose, 5 dose/week. Oligo 1 is AS5-2HM, oligo 2 is anti-mdm2 oligo AS5-2H.

FIG. 16 illustrates the data on in vivo anti-tumor activities of antisense anti-mdm2 oligo AS5-2H administered alone and in combination with HCPT, a DNA damaging agent, into mice bearing SJSA xenografts. At the end of the experiment, tumors were removed and weighed. FIG. 17 illustrates representative tumors from various groups. The results from this study can be summarized as follows: 1) control oligonucleotide AS5-2HM had no effect on tumor growth; 2) AS5-2H had a dose-dependent effect on tumor growth; 3) HCPT had a dose-dependent effect on tumor growth; and 4) co-administration of AS5-2H and HCPT had synergistic effects on tumor growth, but no synergistic effect is seen with control oligo AS5-2HM.

Figure 18A:
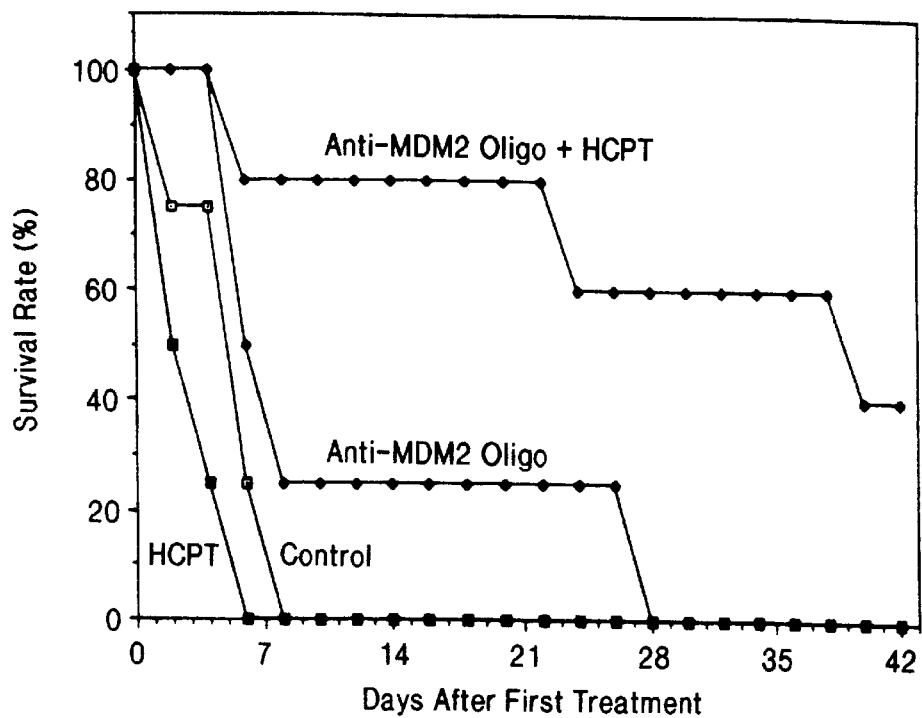
FIG. 18A and 18B display the results of anti-tumor activities of anti-mdm2 oligonucleotides adminstered alone or in combination with topoisomerase I inhibitor HCPT to animals bearing JAR xenografts (average 2,000 mg). Administration was by direct injection into the tupors at the designated daily dose, 5 doses/week. Anti-mdm2 oligonucleotide: AS5-2H (5 mg/kg/day, 5 injections); anti-mdm2 oligonucleotide (5 mg/kg)+HCPT (3 mg/kg); control (saline); HCPT: 3 mg/kg/day.
Figure 18B:
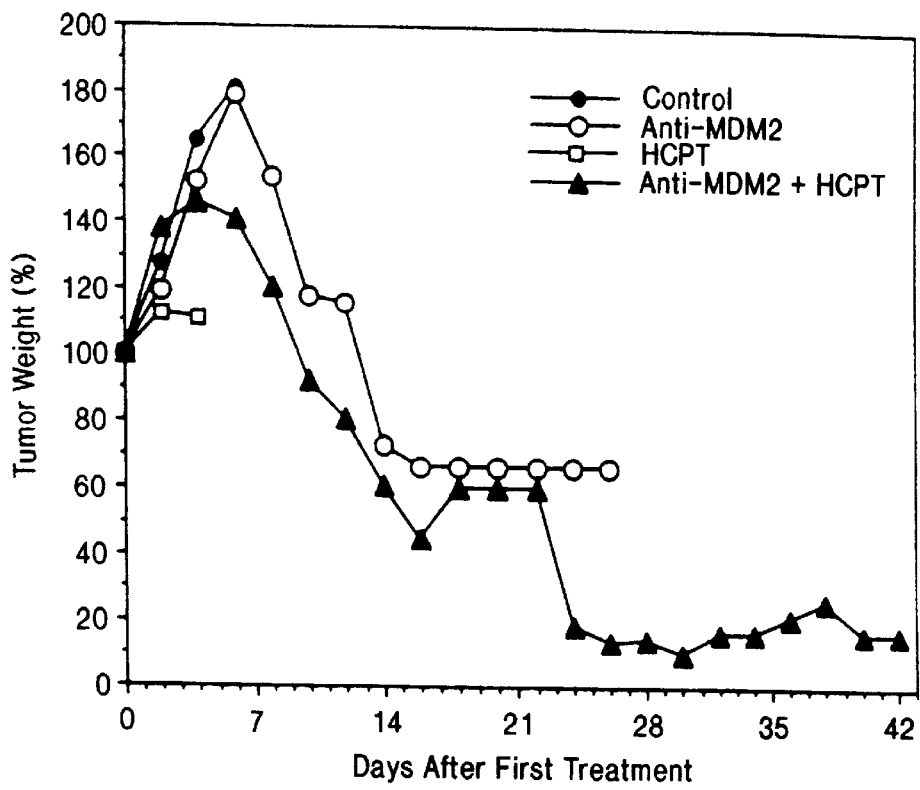

In the studies with JAR xenografts, we took a different approach to investigate the effect of anti-MDM2 oligonucleotides on tumor regression and animal survival. In this case, we directly injected the oligonucleotide AS5-2H or HCPT into large tumors (average 2,000 mg), mimicking the clinical late stage of tumors. The results are depicted in FIG. 18. All control animals died within a week after beginning of treatment. HCPT alone had no effect. 20% of animals treated with anti-mdm2 oligonucleotide survived up to 4 weeks, accompanied by tumor regression. Combination treatment of the anti-mdm2 oligonucleotide and HCPT significantly improved the survival rate: 50% of the animals survived over six weeks with almost complete tumor regression. No significant host toxicity was observed. These results further demonstrate that mdm2 inhibition directly correlates with tumor regression and animal survival.

This is the first direct experimental evidence demonstrating a therapeutic effect by an anti-mdm2 antisense oligonucleotide administered alone or in combination with a DNA damaging agent. These data confirm the findings of the previously presented in vitro studies.

What is claimed is:

1. An antisense oligonucleotide comprising from about 8 to about 50 nucleotides that inhibits MDM2 protein expression, said oligonucleotide binding to mdm2-encoding RNA and being complementary to a sequence that overlaps by at least one nucleotide a sequence within the mdm2 RNA, which sequence within the mdm2 RNA is selected from the group consisting of SEQ ID NOS: 2, 3, 4, 7, 8, 9, 10, and 11.

2. An antisense oligonucleotide comprising from about 8 to about 50 nucleotides that inhibits MDM2 protein expression, said oligonucleotide binding to mdm2-encoding RNA and being complementary to a sequence that overlaps by at least one nucleotide a sequence within the mdm2 RNA, which sequence within the mdm2 RNA is selected from the group consisting of SEQ ID NOS: 13, 14, 15, 16, 17, 18, 19, 20, 21, 22, 23, and 24.

3. The antisense oligonucleotide according to claim 1, said oligonucleotide comprising from about 21 to about 35 nucleotides.

4. The antisense oligonucleotide according to claim 2, said oligonucleotide comprising from about 21 to about 35 nucleotides.

5. The antisense oligonucleotide according to claim 1, said oligonucleotide comprising from about 13 to about 19 nucleotides.

6. The antisense oligonucleotide according to claim 2, said oligonucleotide comprising from about 13 to about 19 nucleotides.

7. The antisense oligonucleotide according to claim 1 that inhibits MDM2 protein expression, said oligonucleotide having the nucleotide base sequence set forth in Sequence Listing as SEQ ID NO:28.

8. The antisense oligonucleotide according to claim 2 that inhibits MDM2 protein expression, said oligonucleotide having the nucleotide base sequence set forth in Sequence Listing as SEQ ID NO:36.

9. The antisense oligonucleotide according to claim 1, having a nucleotide base sequence of an oligonucleotide selected from the group consisting of SEQ ID NOS: 27, 28, 29, 30, 31, 32, 33, and 34.

10. The antisense oligonucleotide according to claim 2, having a nucleotide base sequence of an oligonucleotide selected from the group consisting of SEQ ID NOS: 35, 36, 37, 38, 39, 40, 41, 42, 43, 44, 45, and 46.

11. The oligonucleotide according to claim 1, wherein the oligonucleotide has at least one internucleotide linkage selected from the group consisting of phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleotide linkages.

12. The oligonucleotide according to claim 11, wherein the oligonucleotide is a chimeric oligonucleotide comprising a phosphorothioate, phosphodiester or phosphorodithioate region and an alkylphosphonate or alkylphosphonothioate region.

13. The oligonucleotide according to claim 11, wherein the oligonucleotide comprises a ribonucleotide or 2'-O-substituted ribonucleotide region and a deoxyribonucleotide region.

14. The oligonucleotide according to claim 2, 7, 8, 9, or 10, wherein the oligonucleotide has at least one internucleotide linkage selected from the group consisting of phosphorothioate, phosphorodithioate, siloxane, carbonate, carboxymethylester, acetamidate, carbamate, thioether, bridged phosphoramidate, bridged methylene phosphonate, bridged phosphorothioate, and sulfone internucleotide linkages.

15. The oligonucleotide according to claim 14, wherein the oligonucleotide is a chimeric oligonucleotide comprising a phosphorothioate, phosphodiester, or phosphorodithioate region and an alkylphosphonate or a alkylphosphonothioate region.

16. The oligonucleotide according to claim 14, wherein the oligonucleotide comprises a ribonucleotide or 2'-O-substituted ribonucleotides and the other nucleotides are deoxyribonucleotides.

17. The oligonucleotide according to claim 7, wherein the two terminal 5' nucleotides and the four terminal 3' nucleotides are 2'-O-substituted ribonucleotides and the other nucleotides are deoxyribonucleotides.

18. An oligonucleotide of the structure:

5'-UGACACCTGTTCTCACUCAC-3' (SEQ ID NO: 47) wherein the underlined nucleotides are 2'-O-methyl substituted ribonucleotides and all internucleotide linkages are phosphorothioates.

* * * * *

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 2372 base pairs
      (B) TYPE: nucleic acid
      (C) STRANDEDNESS: both
      (D) TOPOLOGY: linear (ii) MOLECULE TYPE: hmdm2 DNA (iii) HYPOTHETICAL: NO (iv) ANTI-SENSE: NO (xi) SEQUENCE DESCRIPTION: SEQ ID NO:1:

```
GCACCGCGCG AGCTTGGCTG CTTCTGGGGC CTGTGTGGCC CTGTGTGTCG GAAAGATGGA      60

GCAAGAAGCC GAGCCCGAGG GGCGGCCGCG ACCCCTCTGA CCGAGATCCT GCTGCTTTCG     120

CAGCCAGGAG CACCGTCCCT CCCCGGATTA GTGCGTACGA GCGCCCAGTG CCCTGGCCCG     180

GAGAGTGGAA TGATCCCCGA GGCCCAGGGC GTCGTGCTTC CGCAGTAGTC AGTCCCCGTG     240

AAGGAAACTG GGGAGTCTTG AGGGACCCCC GACTCCAAGC GCGAAAACCC CGGATGGTGA     300

GGAGCAGGCA AATGTGCAAT ACCAACATGT CTGTACCTAC TGATGGTGCT GTAACCACCT     360

CACAGATTCC AGCTTCGGAA CAAGAGACCC TGGTTAGACC AAAGCCATTG CTTTTGAAGT     420

TATTAAAGTC TGTTGGTGCA CAAAAAGACA CTTATACTAT GAAAGAGGTT CTTTTTTATC     480

TTGGCCAGTA TATTATGACT AAACGATTAT ATGATGAGAA GCAACAACAT ATTGTATATT     540

GTTCAAATGA TCTTCTAGGA GATTTGTTTG GCGTGCCAAG CTTCTCTGTG AAAGAGCACA     600

GGAAAATATA TACCATGATC TACAGGAACT TGGTAGTAGT CAATCAGCAG GAATCATCGG     660

ACTCAGGTAC ATCTGTGAGT GAGAACAGGT GTCACCTTGA AGGTGGGAGT GATCAAAAGG     720

ACCTTGTACA AGAGCTTCAG GAAGAGAAAC CTTCATCTTC ACATTTGGTT TCTAGACCAT     780

CTACCTCATC TAGAAGGAGA GCAATTAGTG AGACAGAAGA AAATTCAGAT GAATTATCTG     840

GTGAACGACA AAGAAAACGC CACAAATCTG ATAGTATTTC CCTTTCCTTT GATGAAAGCC     900

TGGCTCTGTG TGTAATAAGG GAGATATGTT GTGAAAGAAG CAGTAGCAGT GAATCTACAG     960

GGACGCCATC GAATCCGGAT CTTGATGCTG GTGTAAGTGA ACATTCAGGT GATTGGTTGG    1020

ATCAGGATTC AGTTTCAGAT CAGTTTAGTG TAGAATTTGA AGTTGAATCT CTCGACTCAG    1080

AAGATTATAG CCTTAGTGAA GAAGGACAAG AACTCTCAGA TGAAGATGAT GAGGTATATC    1140

AAGTTACTGT GTATCAGGCA GGGGAGAGTG ATACAGATTC ATTTGAAGAA GATCCTGAAA    1200

TTTCCTTAGC TGACTATTGG AAATGCACTT CATGCAATGA AATGAATCCC CCCCTTCCAT    1260
```

-continued

```
CACATTGCAA CAGATGTTGG GCCCTTCGTG AGAATTGGCT TCCTGAAGAT AAAGGGAAAG    1320

ATAAAGGGGA AATCTCTGAG AAAGCCAAAC TGGAAAACTC AACACAAGCT GAAGAGGGCT    1380

TTGATGTTCC TGATTGTAAA AAAACTATAG TGAATGATTC CAGAGAGTCA TGTGTTGAGG    1440

AAAATGATGA TAAAATTACA CAAGCTTCAC AATCACAAGA AAGTGAAGAC TATTCTCAGC    1500

CATCAACTTC TAGTAGCATT ATTTATAGCA GCCAAGAAGA TGTGAAAGAG TTTGAAAGGG    1560

AAGAAACCCA AGACAAAGAA GAGAGTGTGG AATCTAGTTT GCCCCTTAAT GCCATTGAAC    1620

CTTGTGTGAT TTGTCAAGGT CGACCTAAAA ATGGTTGCAT TGTCCATGGC AAAACAGGAC    1680

ATCTTATGGC CTGCTTTACA TGTGCAAAGA AGCTAAAGAA AAGGAATAAG CCCTGCCCAG    1740

TATGTAGACA ACCAATTCAA ATGATTGTGC TAACTTATTT CCCCTAGTTG ACCTGTCTAT    1800

AAGAGAATTA TATATTTCTA ACTATATAAC CCTAGGAATT TAGACAACCT GAAATTTATT    1860

CACATATATC AAAGTGAGAA AATGCCTCAA TTCACATAGA TTTCTTCTCT TTAGTATAAT    1920

TGACCTACTT TGGTAGTGGA ATAGTGAATA CTTACTATAA TTTGACTTGA ATATGTAGCT    1980

CATCCTTTAC ACCAACTCCT AATTTTAAAT AATTTCTACT CTGTCTTAAA TGAGAAGTAC    2040

TTGGTTTTTT TTTTCTTAAA TATGTATATG ACATTTAAAT GTAACTTATT ATTTTTTTTG    2100

AGACCGAGTC TTGCTCTGTT ACCCAGGCTG GAGTGCAGTG GGTGATCTTG GCTCACTGCA    2160

AGCTCTGCCC TCCCCGGGTT CGCACCATTC TCCTGCCTCA GCCTCCCAAT TAGCTTGGCC    2220

TACAGTCATC TGCCACCACA CCTGGCTAAT TTTTTGTACT TTTAGTAGAG ACAGGGTTTC    2280

ACCGTGTTAG CCAGGATGGT CTCGATCTCC TGACCTCGTG ATCCGCCCAC CTCGGCCTCC    2340

CAAAGTGCTG GGATTACAGG CATGAGCCAC CG                                  2372
```

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:2:

```
TTGGCCAGTA TATTATGACT                                                  20
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:3:

```
CCTTGAAGGT GGGAGTGATC                                                  20
```

(2) INFORMATION FOR SEQ ID NO:4:

```
    (i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:4:

TGGATCAGGA TTCAGTTTCA                                              20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:5:

GATGACTCAC ACCATCATGG                                              20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:6:

CAGAGCCTTC ATCTTCCCAG                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:7:

ACCTCACAGA TTCCAGCTTC                                              20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: both
```

(D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:8:

CCAGCTTCGG AACAAGAGAC                                                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:9:

TCTACCTCAT CTAGAAGGAG                                                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:10:

TCCTTAGCTG ACTATTGGAA                                                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:11:

TCATGCAATG AAATGAATCC                                                    20

(2) INFORMATION FOR SEQ ID NO:12:

(i) SEQUENCE CHARACTERISTICS:
        (A) LENGTH: 1710 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:12:

| | | | | | |
|---|---|---|---|---|---|
| GAGGAGCCGC | CGCCTTCTCG | TCGCTCGAGC | TCTGGACGAC | CATGGTCGCT | CAGGCCCCGT | 60 |
| CCGCGGGGCC | TCCGCGCTCC | CCGTGAAGGG | TCGGAAGATG | CGCGGGAAGT | AGCAGCCGTC | 120 |
| TGCTGGGCGA | GCGGGAGACC | GACCGGACAC | CCCTGGGGGA | CCCTCTCGGA | TCACCGCGCT | 180 |
| TCTCCTGCGG | CCTCCAGGCC | AATGTGCAAT | ACCAACATGT | CTGTGTCTAC | CGAGGGTGCT | 240 |
| GCAAGCACCT | CACAGATTCC | AGCTTCGGAA | CAAGAGACTC | TGGTTAGACC | AAAACCATTG | 300 |
| CTTTTGAAGT | TGTTAAAGTC | CGTTGGAGCG | CAAAACGACA | CTTACACTAT | GAAAGAGATT | 360 |
| ATATTTTATA | TTGGCCAGTA | TATTATGACT | AAGAGGTTAT | ATGACGAGAA | GCAGCAGCAC | 420 |
| ATTGTGTATT | GTTCAAATGA | TCTCCTAGGA | GATGTGTTTG | GAGTCCCGAG | TTTCTCTGTG | 480 |
| AAGGAGCACA | GGAAAATATA | TGCAATGATC | TACAGAAATT | TAGTGGCTGT | AAGTCAGCAA | 540 |
| GACTCTGGCA | CATCGCTGAG | TGAGAGCAGA | CGTCAGCCTG | AAGGTGGGAG | TGATCTGAAG | 600 |
| GATCCTTTGC | AAGCGCCACC | AGAAGAGAAA | CCTTCATCTT | CTGATTTAAT | TTCTAGACTG | 660 |
| TCTACCTCAT | CTAGAAGGAG | ATCCATTAGT | GAGACAGAAG | AGAACACAGA | TGAGCTACCT | 720 |
| GGGGAGCGGC | ACCGGAAGCG | CCGCAGGTCC | CTGTCCTTTG | ATCCGAGCCT | GGGTCTGTGT | 780 |
| GAGCTGAGGG | AGATGTGCAG | CGGCGGCACG | AGCAGCAGTA | GCAGCAGCAG | CAGCGAGTCC | 840 |
| ACAGAGACGC | CCTCGCATCA | GGATCTTGAC | GATGGCGTAA | GTGAGCATTC | TGGTGATTGC | 900 |
| CTGGATCAGG | ATTCAGTTTC | TGATCAGTTT | AGCGTGGAAT | TTGAAGTTGA | GTCTCTGGAC | 960 |
| TCGGAAGATT | ACAGCCTGAG | TGACGAAGGG | CACGAGCTCT | CAGATGAGGA | TGATGAGGTC | 1020 |
| TATCGGGTCA | CAGTCTATCA | GACAGGAGAA | AGCGATACAG | ACTCTTTTGA | AGGAGATCCT | 1080 |
| GAGATTTCCT | TAGCTGACTA | TTGGAAGTGT | ACCTCATGCA | ATGAAATGAA | TCCTCCCCTT | 1140 |
| CCATCACACT | GCAAAAGATG | CTGGACCCTT | CGTGAGAACT | GGCTTCCAGA | CGATAAGGGG | 1200 |
| AAAGATAAAG | TGGAAATCTC | TGAAAAAGCC | AAACTGGAAA | ACTCAGCTCA | GGCAGAAGAA | 1260 |
| GGCTTGGATG | TGCCTGATGG | CAAAAAGCTG | ACAGAGAATG | ATGCTAAAGA | GCCATGTGCT | 1320 |
| GAGGAGGACA | GCGAGGAGAA | GGCCGAACAG | ACGCCCCTGT | CCCAGGAGAG | TGACGACTAT | 1380 |
| TCCCAACCAT | CGACTTCCAG | CAGCATTGTT | TATAGCAGCC | AAGAAAGCGT | GAAAGAGTTG | 1440 |
| AAGGAGGAAA | CGCAGCACAA | AGACGAGAGT | GTGGAATCTA | GCTTCTCCCT | GAATGCCATC | 1500 |
| GAACCATGTG | TGATCTGCCA | GGGGCGGCCT | AAAAATGGCT | GCATTGTTCA | CGGCAAGACT | 1560 |
| GGACACCTCA | TGTCATGTTT | CACGTGTGCA | AAGAAGCTAA | AAAAAAGAAA | CAAGCCCTGC | 1620 |
| CCAGTGTGCA | GACAGCCAAT | CCAAATGATT | GTGCTAAGTT | ACTTCAACTA | GCTGACCTGC | 1680 |
| TCACAAAAAT | AGAATTTTAT | ATTTCTAACT | | | | 1710 |

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:13:

ACATCTGTGA GTGAGAACAG                    20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:14:

GTGAGTGAGA ACAGGTGTCA                    20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:15:

TGAGAACAGG TGTCACCTTG                    20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:16:

ACAGGTGTCA CCTTGAAGGT                    20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:17:

TGGGAGTGAT CAAAAGGACC                    20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:18:

GTGATCAAAA GGACCTTGTA                               20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:19:

AAGGACCTTG TACAAGAGCT                               20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:20:

TGAACATTCA GGTGATTGGT                               20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:21:

ATTCAGGTGA TTGGTTGGAT                               20

(2) INFORMATION FOR SEQ ID NO:22:

(i) SEQUENCE CHARACTERISTICS:
        (A) LENGTH: 21 base pairs

```
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:22:

AGGTGATTGG TTGGATCAGG A                                          21

(2) INFORMATION FOR SEQ ID NO:23:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:23:

ATTCAGTTTC AGATCAGTTT                                            20

(2) INFORMATION FOR SEQ ID NO:24:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:24:

GATCAGTTTA GTGTAGAATT                                            20

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:25:

TGACACTTGT TCTTACTCAC                                            20

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: both
            (D) TOPOLOGY: linear
```

(ii) MOLECULE TYPE: nucleic acid (iii) HYPOTHETICAL: NO (iv) ANTI-SENSE: YES (xi) SEQUENCE DESCRIPTION: SEQ ID NO:26:

TGACTCTTGT CCTTACTCAC                                               20

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:27:

AGTCATAATA TACTGGCCAA                                               20

(2) INFORMATION FOR SEQ ID NO:28:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:28:

GATCACTCCC ACCTTCAAGG                                               20

(2) INFORMATION FOR SEQ ID NO:29:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:29:

TGAAACTGAA TCCTGATCCA                                               20

(2) INFORMATION FOR SEQ ID NO:30:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:30:

GAAGCTGGAA TCTGTGAGGT                                      20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:31:

GTCTCTTGTT CCGAAGCTGG                                      20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:32:

CTCCTTCTAG ATGAGGTAGA                                      20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:33:

TTCCAATAGT CAGCTAAGGA                                      20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:34:

```
GGATTCATTT CATTGCATGA                                               20
```

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:35:

```
CTGTTCTCAC TCACAGATGT                                               20
```

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:36:

```
TGACACCTGT TCTCACTCAC                                               20
```

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:37:

```
CAAGGTGACA CCTGTTCTCA                                               20
```

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:38:

```
ACCTTCAAGG TGACACCTGT                                               20
```

(2) INFORMATION FOR SEQ ID NO:39:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:39:

GGTCCTTTTG ATCACTCCCA                                                      20

(2) INFORMATION FOR SEQ ID NO:40:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:40:

TACAAGGTCC TTTTGATCAC                                                      20

(2) INFORMATION FOR SEQ ID NO:41:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:41:

AGCTCTTGTA CAAGGTCCTT                                                      20

(2) INFORMATION FOR SEQ ID NO:42:

(i) SEQUENCE CHARACTERISTICS:
            (A) LENGTH: 20 base pairs
            (B) TYPE: nucleic acid
            (C) STRANDEDNESS: both
            (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:42:

ACCAATCACC TGAATGTTCA                                                      20

(2) INFORMATION FOR SEQ ID NO:43:

(i) SEQUENCE CHARACTERISTICS:
            (A) LENGTH: 20 base pairs
            (B) TYPE: nucleic acid

```
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:43:

ATCCAACCAA TCACCTGAAT                                            20

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:44:

TCCTGATCCA ACCAATCACC T                                          21

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:45:

AAACTGATCT GAAACTGAAT                                            20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:46:

AATTCTACAC TAAACTGATC                                            20

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid
```

```
    (iii) HYPOTHETICAL: NO (iv) ANTI-SENSE: YES (xi) SEQUENCE DESCRIPTION: SEQ ID NO:47:

UGACACCTGT TCTCACUCAC                                              20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:48:

UGAGACCAGT TGTCAGUCAC                                              20

(2) INFORMATION FOR SEQ ID NO:49:

(i) SEQUENCE CHARACTERISTICS:
        (A) LENGTH: 73 base pairs
        (B) TYPE: nucleic acid
        (C) STRANDEDNESS: both
        (D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:49:

AAGCTCTTGT ACAAGGTCCT TTTGATCACT CCCACCTTCA AGGTGACACC TGTTCTCACT   60

CACAGATGTA CCT                                                     73
```